United States Patent
Tracey et al.

(10) Patent No.: US 10,857,197 B2
(45) Date of Patent: Dec. 8, 2020

(54) TREATMENT OF HMGB1-MEDIATED INFLAMMATION

(71) Applicant: The Feinstein Institue for Medical Research, Great Neck, NY (US)

(72) Inventors: Kevin J. Tracey, Great Neck, NY (US); Huan Yang, Manhasset, NY (US); Yousef Al-Abed, Manhasset, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 217 days.

(21) Appl. No.: 15/532,226

(22) PCT Filed: Dec. 14, 2015

(86) PCT No.: PCT/US2015/065521
§ 371 (c)(1),
(2) Date: Aug. 21, 2018

(87) PCT Pub. No.: WO2016/094899
PCT Pub. Date: Jun. 16, 2016

(65) Prior Publication Data
US 2018/0353564 A1  Dec. 13, 2018

Related U.S. Application Data

(60) Provisional application No. 62/222,486, filed on Sep. 23, 2015, provisional application No. 62/090,934, filed on Dec. 12, 2014.

(51) Int. Cl.
| | |
|---|---|
| *A61K 38/07* | (2006.01) |
| *A61K 38/04* | (2006.01) |
| *C07K 5/00* | (2006.01) |
| *A61P 29/00* | (2006.01) |
| *A61K 31/7024* | (2006.01) |
| *A61K 31/215* | (2006.01) |
| *C07K 5/107* | (2006.01) |

(52) U.S. Cl.
CPC ............ *A61K 38/07* (2013.01); *A61K 31/215* (2013.01); *A61K 31/7024* (2013.01); *A61P 29/00* (2018.01); *C07K 5/1016* (2013.01)

(58) Field of Classification Search
None
See application file for complete search history.

(56) References Cited

U.S. PATENT DOCUMENTS

| | | |
|---|---|---|
| 2006/0121047 A1 | 6/2006 | Tracey |
| 2006/0275295 A1 | 12/2006 | Jullien et al. |
| 2013/0143747 A1 | 6/2013 | Gutin et al. |
| 2013/0281395 A1 | 10/2013 | Wipf et al. |

FOREIGN PATENT DOCUMENTS

| | | |
|---|---|---|
| CN | 101245098 A | 7/2007 |
| WO | 00/41703 A1 | 7/2000 |
| WO | 2009/152517 A1 | 12/2009 |
| WO | 2013/148072 A1 | 10/2013 |

OTHER PUBLICATIONS

McDonald et al., Mol. Med. 20:639-648 (first available Oct. 31, 2014) (Year: 2014).*
Wang et al., Hepatology 57:373-384 (2013) (Year: 2013).*
Sun et al., PLos ONE 13:e0193028 (2018) (Year: 2018).*
Dimitropoulos et al., "Acetaminophen Toxicity: What Pharmacists Need to Know," available online at https://www.uspharmacist.com/article/acetaminophen-toxicity-what-pharmacists-need-to-know, 13 pages (2014) (Year: 2014).*
Grinnan et al., Am. J. Resp. Crit. Care Med. 199:1460-1461 (2019) (Year: 2019).*
VanPatten et al., J. Med. Chem. 61:5093-5107 (2018) (Year: 2018).*
Yang et al., Mol. Med. 8:250-259 (2012) (Year: 2012).*
HMGBiotech, "HMGB1 Isoforms Kit," available online at http://hmgbiotech.eu/wp-content/uploads/2018/06/isoformnew.pdf, 4 pages (accessed on Sep. 20, 2019) (Year: 2019).*
PubChem Database, PubChem CID No. 6912404, available online at https://pubchem.ncbi.nlm.nih.gov/compound/Eritoran, 18 pages (2006) (Year: 2006).*
Andersson, Ulf, and Kevin J. Tracey. "HMGB1 is a therapeutic target for sterile inflammation and infection." Annual review of immunology 29 (2011): 139-162.
Chen, Grace Y., and Gabriel Nuñez. "Sterile inflammation: sensing and reacting to damage." Nature Reviews Immunology 10.12 (2010): 826.
Fisher, James E., et al. "Role of Kupffer cells and toll-like receptor 4 in acetaminophen-induced acute liver failure." journal of surgical research 180.1 (2013): 147-155.
Slivka, Peter F., et al. "A peptide antagonist of the TLR4-MD2 interaction." Chembiochem 10.4 (2009): 645-649.
Whitley, Richard J., et al. "Oral oseltamivir treatment of influenza in children." The Pediatric infectious disease journal 20.2 (2001): 127-133.
Yang, Huan, et al. "MD-02 is required for disulfide HMGB1-dependent TLR4 signaling." Journal of Experimental Medicine (2015): jem-20141318.
Yang, Huan, and Kevin J. Tracey. "Targeting HMGB1 in inflammation." Biochimica et Biophysica Acta (BBA)—Gene Regulatory Mechanisms 1799.1-2 (2010): 149-156.
European Search Report for corresponding European Patent Application Serial No. 15867456.4, dated Jun. 25, 2018, pp. 1-13.

* cited by examiner

*Primary Examiner* — Thea D'Ambrosio
(74) *Attorney, Agent, or Firm* — Tarolli, Sundheim, Covell & Tummino LLP

(57) ABSTRACT

Methods of treating HMGB1-mediated inflammation by administering a therapeutically effective amount of an MD2-antagonist to a subject in need thereof are described. The novel MD2 antagonist tetrapeptide P5779 is also described.

12 Claims, 11 Drawing Sheets

Specification includes a Sequence Listing.

TREATMENT OF HMGB1-MEDIATED INFLAMMATION

CROSS-REFERENCE TO RELATED APPLICATIONS

This application is being submitted under 35 U.S.C. § 371 and claims priority from International Application Serial No. PCT/US2015/065521, which claims priority to U.S. Provisional Patent Application Ser. No. 62/090,934, filed Dec. 12, 2014, and U.S. Provisional Patent Application Ser. No. 62/222,486, filed Sep. 23, 2015, all of which are incorporated herein by reference.

GOVERNMENT FUNDING

This invention was made with Government support under grant numbers GM062508, GM098446, GM053789, and AT005076 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Dec. 14, 2015, is named HMGB1 NSLIJ-024062_ST25 and is 4,096 bytes in size.

BACKGROUND

Following infection or injury, the immediate host inflammatory response is mediated by receptors on innate immune cells that can efficiently recognize pathogen- or damage-associated molecular patterns (PAMPs or DAMPs). For instance, the mammalian response to bacterial endotoxin (lipopolysaccharide, LPS) is mediated by the LPS-binding protein (LBP), CD14, MD2, and TLR4. Upon capturing LPS, LBP transfers it to CD14 and MD2, which then delivers LPS to the signaling, high-affinity transmembrane Toll-like receptor 4 (TLR4). Nagai et al., Nat Immunol 3:667-672 (2002). The engagement of LPS with TLR4 triggers the sequential release of "early" (e.g., TNF, IL-1, IFN-β) and "late" pro-inflammatory mediators (e.g., HMGB1) Wang et al., Science 285:248-251 (1999).

As a ubiquitous nuclear protein, HMGB1 can be passively released from damaged cells following sterile tissue injury due to ischemia/reperfusion (Tsung et al., J Exp Med 201: 1135-1143 (2005)) or chemical toxicity. Antoine et al., Hepatology 58:777-787 (2013). HMGB1 can signal through a family of receptors including RAGE, TLR4, and cluster of differentiation 24 (CD24)/Siglec-10, thereby functioning as a DAMP that alerts, recruits and activates innate immune cells to produce a wide range of cytokines and chemokines. Thus, seemingly unrelated conditions such as infection and sterile injury can converge on a common process: inflammation, which is orchestrated by HMGB1 actively secreted from innate immune cells or passively released from damaged tissues. Andersson, U. and Tracey, K. J., Annu Rev Immunol 29:139-162 (2011). Extracellular HMGB1 has been established as a pathogenic mediator of both infection- and injury-elicited inflammatory diseases. Yang et al., J Leukoc Biol 93:865-873 (2013).

HMGB1 is a redox-sensitive protein as it contains three conserved cysteine residues at position 23, 45 and 106. The redox status of the cysteines dictates its extracellular chemokine or cytokine-inducing properties. Specifically, HMGB1 with all cysteine residues reduced (fully reduced HMGB1) binds to CXCL12 and stimulates immune cell infiltration via the CXCR4 receptor in a synergistic fashion. Partially oxidized HMGB1, with a Cys23-Cys45 disulfide bond and a reduced Cys106 (disulfide HMGB1), activates immune cells to produce cytokines/chemokines via the TLR4 receptor. Once all cysteines are terminally oxidized (sulfonyl HMGB1), HMGB1 is devoid of chemotactic and cytokine activities. Previously we showed that HMGB1 induces inflammatory responses via the TLR4/MD2 signaling pathway, and that the interaction with TLR4/MD2 requires a specific HMGB1 redox form with a distinct atomic structure of thiol-cysteine 106. Yang et al., Mol Med 18:250-259 (2012). Ample evidence suggests that HMGB1, when actively secreted by activated immune cells or passively released from dying cells, is a mixture of several isoforms with distinct post-translational modifications. Paradoxically, it is unknown how the immune system uses the TLR4/MD2 receptor system to distinguish between different isoforms of HMGB1, specifically recognizing the disulfide HMGB1 molecule to the exclusion of other isoforms.

A type HMGB1-mediated inflammation that is of particular interest is that caused by Influenza. Influenza continues to evolve with new antigenic variants emerging annually, as exemplified by the last several influenza seasons in which the recommended vaccine was considerably less efficacious than predicted. Therefore, there remains a pressing need to develop alternatives to the annual influenza vaccines and anti-viral agents currently used to mitigate the effects of influenza infection. Influenza virus is sensed by multiple PRRs, including TLR3, TLR7, TLR8, TLR10, and the intra-cytosolic sensor, RIG-I, although TLR8 and TLR10 are not functional in mice. CD14 is required for influenza-induced cytokine production by mouse macrophages, independent of TLR2 and TLR4. In addition, $MyD88^{-/-}$ and MyD88/TRIF double deficient mice show a dramatic reduction of pulmonary cytokine production when compared to WT mice, indicating the important role of these TLR signaling pathways in disease.

Imai et al. proposed that chemical or microbial insults trigger NADPH-dependent reactive oxygen species that generate a host-derived oxidized phospholipid, oxidized 1-palmitoyl-2-arachidonoyl-phosphaticylcholine (OxPAPC), in lungs. Imai et al., Cell 133, 235-249 (2008). They concluded that regardless of the initial sensing involved in pathogen recognition, OxPAPC initiates a common TLR4-, TRIF-, and IL-6-dependent pathway in macrophages that leads to ALI. We showed that treatment of influenza-infected mice with Eritoran, the most potent, synthetic lipid A analog known (Lien et al., J. Biol. Chem. 276, 1873-1880 (2001)), blocked influenza-induced lethality and ALI. When administered daily to WT mice for 5 days, starting on days 2, 4, or 6 post-infection, Eritoran treatment significantly improved survival and clinical symptoms, while decreasing ALI, OxPAPC accumulation, the cytokine storm, and systemic inflammation. Shirey et al., Nature 497, 498-502 (2013).

SUMMARY OF THE INVENTION

The present invention provides methods of treating or preventing HMGB1-mediated inflammation in a subject, by administering a therapeutically effective amount of an MD2-antagonist to a subject in need thereof. In some embodiments, the HMGB1 is the HMGB1 disulfide isoform. When treating HMGB1-mediated inflammation, the MD2-antagonist is administered after the onset of infection in some embodiments. In some embodiments, the MD2-antagonist is administered in a pharmaceutically acceptable carrier.

HMGB1-mediated inflammation can result from infection or sterile injury. In some embodiments, the HMGB1-mediated inflammation is caused by viral infection, such as influenza infection. In some embodiments, when treating HMGB1 inflammation that is caused by viral infection, the method further comprises administering an anviral agent (e.g., oseltamivir) to the subject. In other embodiments, the HMGB1-mediated inflammation is caused by bacterial infection. In further embodiments, the HMGB1-mediated inflammation is caused by sterile injury, such as acetaminophen toxicity.

Another aspect of the invention provides a composition comprising the MD2 antagonist having the amino acid sequence FSSE (SEQ ID NO: 1). In some embodiments, the MD2 antagonist composition further comprises a pharmaceutically acceptable carrier.

BRIEF DESCRIPTION OF THE FIGURES

The present invention may be more readily understood by reference to the following figures, wherein.

DETAILED DESCRIPTION OF THE INVENTION

Figure 1:
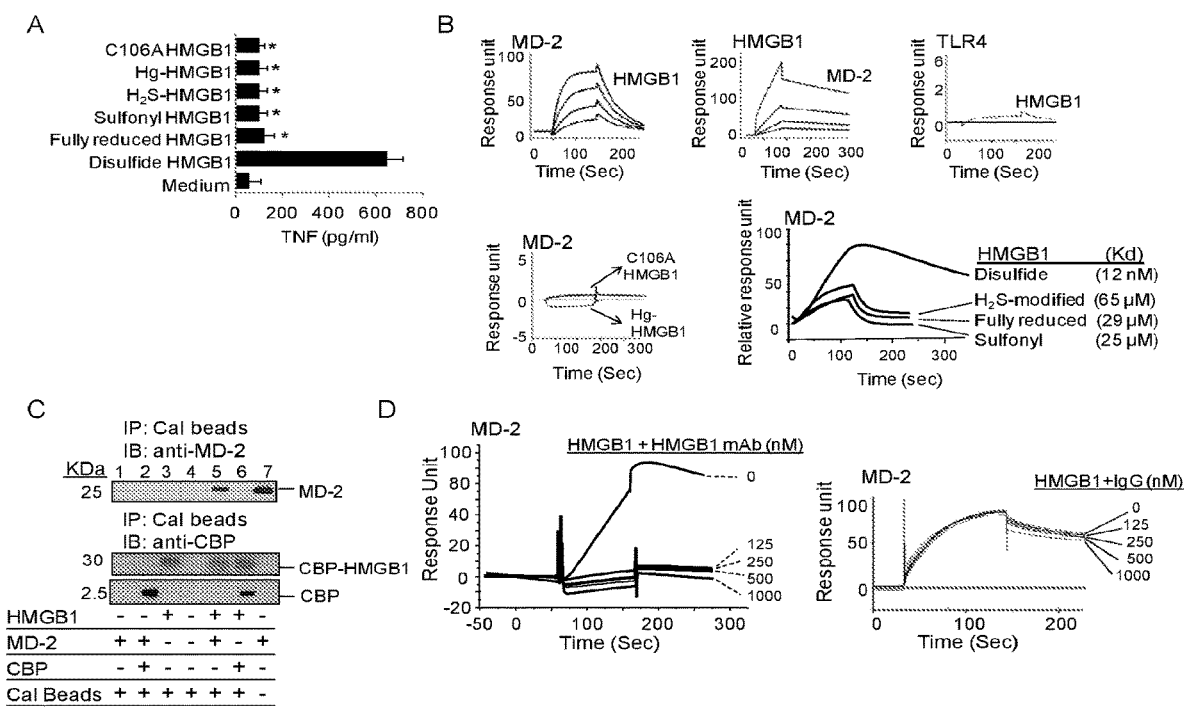
FIGS. 1A-1D provide graphs showing disulfide HMGB1 binds to MD2. (A) TNF release was measured from RAW 264.7 cells stimulated with various isoforms of HMGB1 as indicated (1 μg/ml, 16 h). *: P<0.05 vs. disulfide HMGB1. N=3-5 experiments. (B) Surface plasmon resonance (SPR, BIAcore) analysis was performed to assess HMGB1 binding to MD2 or TLR4 (coated on the chip). Upper row: HMGB1 binding to human MD2 was tested at different HMGB1 concentrations (12.5, 25, 50 and 100 nM) with an apparent Kd of 12 nM (left graph). Human MD2 (12.5, 25, 50 and 100 nM) binding to HMGB1 (coated on the chip, middle graph); disulfide HMGB1 (100 nM) was tested binding to TLR4 (coated on the chip, right graph). Lower row: Non-cytokine-inducing HMGB1 (C106A, Hg-HMGB1, 1 μM) were tested binding to MD2 (coated on the chip, left graph). HMGB1 isoforms were tested for binding to MD2 (coated on the chip, right graph). Data are presented as response units (RU) or relative RU over time (seconds) and representative of three experiments. (C) Mixture of CBP-tagged HMGB1 or CBP alone with supernatant of yeast Sf9 cells expressing MD2 was immune-precipitated with calmodulin beads (immune-precipitation, IP), and immunoblotted (IB) with anti-human MD2 or CBP antibodies. Recombinant MD2 protein was included as positive control (right lane). Data shown are representative of 3 repeats. (D) SPR analysis of HMGB1 binding to human MD2 (coated on the chip) was performed in the presence of monoclonal anti-HMGB1 mAb (left graph) or irrelevant mouse IgG (right graph) as shown. Data are representative of 3 repeats.

The inventors have described a method of treating HMGB1-mediated inflammation in a subject by administering a therapeutically effective amount of an MD2-antagonist to a subject in need thereof.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

Treat", "treating", and "treatment", etc., as used herein, refer to any action providing a benefit to a subject afflicted with HMGB1-mediated inflammation, including improvement in the condition through lessening or suppression of at least one symptom, delay in progression of the disease or condition, etc.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as non-proteinogenic).

The following abbreviations are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine.

"Pharmaceutically acceptable" as used herein means that the compound or composition is suitable for administration to a subject for the methods described herein, without unduly deleterious side effects in light of the severity of the disease and necessity of the treatment.

The term "therapeutically effective" is intended to qualify the amount of each agent which will achieve the goal of decreasing disease severity while avoiding adverse side effects such as those typically associated with alternative therapies. The therapeutically effective amount may be administered in one or more doses. An effective dose, on the other hand, is an amount sufficient to provide a certain effect, such as enzyme inhibition, but may or may not be therapeutically effective.

Methods of Treating HMGB1-Mediated Inflammation

In one aspect, the present invention provides methods of treating HMGB1-mediated inflammation in a subject, by administering a therapeutically effective amount of an MD2-antagonist to a subject in need thereof. High mobility group box 1 protein (HMGB1) is a mediator of both infection- and injury-elicited inflammatory diseases and conditions. Activated macrophages and monocytes secrete HMGB1 as a cytokine mediator of Inflammation. HMGB1 is also known as high-mobility group protein 1 (HMG-1) and amphoterin, and is encoded by the HMGB1 gene. Several different isoforms of HMGB1 with distinct post-translational modifications are involved in inflammation. Accordingly, in some embodiments, the HMGB1-mediated disease is mediated by one or more HMGB1 isoforms. For example, in some embodiments, the HMGB1 is the HMGB1 disulfide isoform.

HMGB1-mediated inflammation, as defined herein, is a disease or condition in HMGB1 plays a significant role in the pathology of the disease. As further described herein, HMGB1 is secreted by immune cells such as macrophages, monocytes and dendritic cells as a cytokine mediator of Inflammation. HMGB1 induces inflammatory responses via the TLR4/MD2 signaling pathway as a result of binding to TLR4, which mediates HMGB1-dependent activation of macrophage cytokine release. As a result, HMGB1 is involved in both sterile and infectious inflammatory responses.

Inflammatory disease includes a wide variety of disorders characterized by pathological inflammation of tissue. Immunoactivation, which evolved as a system of host defense against pathogens, can become dysregulated and promote the pathogenesis of diverse diseases with both known and unknown etiologies Immunoactivation and associated inflammation seems to be a "common denominator" or general mechanism of pathogenesis and may explain the association and similarities in pathology among otherwise unrelated human diseases. Margolis, L., Am J Med. 128(6): 562-6 (2015). Examples of inflammatory disease include Acne vulgaris, Sepsis, Asthma, Celiac disease, Chronic prostatitis, Glomerulonephritis, Inflammatory bowel diseases, Pelvic inflammatory disease, Ischemia-Reperfusion injury, Rheumatoid arthritis, Sarcoidosis, Vasculitis, house dust mite-induced airway inflammation, and Interstitial cystitis. HMGB1 plays an important role in these inflammatory responses for all of these diseases. See Yang et al., Mol Med 21:S6-S12 (2015); Kang et al. Mol Aspects Med. 1-116 (2014); Andersson et al., Annual Rev Immunol 29:139-62 (2011).

In some embodiments, the HMGB1-mediated inflammation is due infection. Inflammation plays an important role in protection against infection, and involves eliminating the initial cause of cell injury, clearing out necrotic cells and tissues damaged from the original insult and the inflammatory process, and to initiating tissue repair. However, in some cases, infection can induce excessive and potentially dangerous inflammation. For example, viral triggering of cytokine-mediated lung inflammation can play a significant role in virulence of infection. Likewise, endotoxins resulting from bacterial infection can cause sepsis, which is a form of HMGB1-mediated inflammation.

HMGB1-mediated inflammation can result from various types of infection. For example, in some embodiments, HMGB1-mediated inflammation is caused by viral infection. Examples of viruses that can cause pathological inflammation include, for example, dengue virus, Hepatitis B virus (Cao et al, Sci Rep. 5:14240-5, 2015), influenza A virus (H1N1) (Nosaka et al., Critical Care, 19:249-258, 2015), chicken infectious anemia virus (Sawant et al., Vaccine. 33:333-40, 2015), human papillomavirus (Weng et al., Mol Med Rep. 10:1765-71, 2014). In some embodiments, the HMGB1-mediated inflammation is caused by influenza infection, which frequently causes pathological inflammation.

In other embodiments, the HMGB1-mediated inflammation is caused by bacterial infection. Pathological inflammation can occur as a result of infection by a wide variety of different types of bacteria. Examples of bacteria that can trigger a pathological inflammation response include *Mycobacterium tuberculosis*, bacterium *Burkholderia pseudomallei*, bacterium *Francisella tularensis* (Kang et al., Mol Aspects Med. 1-116, 2014; Laws et al., Internation J of Infect Dis 40:1-8, 2015. D'Elia R V et al., Antimicrob Agents Chemother June issue PMCID: PMC3754292, 2013), *Pseudomonas aeruginosa*, Gram-negative pathogen-induced Keratitis (McClellan et al., J Immunol. 194:1776-1787, 2015).

Alternately, in some embodiments, HMGB1-mediated inflammation is caused by factors other than infection. Inflammation caused by factors other than infection is referred to herein as inflammation resulting from "sterile injury." Sterile injury can trigger an acute inflammatory response, which might be responsible for the pathogenesis of several diseases, including rheumatoid arthritis, lung fibrosis and acute liver failure. Examples of sterile inflammation include acetaminophen toxicity, wound healing, rheumatoid arthritis, hemorrhagic shock, myocardial infarction, ischemia-reperfusion injury and transplantation, cerebral ischemia and injury (Kang et al., Mol Aspects Med. 1-116, 2014. Andersson et al., Annual Rev Immunol 29:139-62, 2011, Yang et al., Mol Med 21:S6-S12, 2015). In some embodiments, the HMGB1-mediated inflammation is caused by acetaminophen toxicity.

MD2-Antagonists

A preferred method of treating HMGB1-mediated inflammation in a subject is administration of a therapeutically effective amount of a myeloid differentiation protein 2 (MD2) antagonist to the subject. One of the advantages of treatment in an MD2 antagonist over many other methods of treating inflammation is that treatment with an MD2 antagonist does not substantially decrease anti-microbial immune responsiveness.

An MD2 antagonist is a compound which interferes with the activity of MD2. For example, an MD2 antagonist can interfere with the binding between MD2 and another peptide, such as TLR4 or HMGB1. Hawkins et al. described Eritoran and related compounds, which are lipid-based compounds that can be used as MD2 antagonists. Hawkins et al., Curr Top Med Chem. 4(11):1147-71 (2004). Another MD2-antagonist, identified by the inventors, is P5779, which is a tetrapeptide having the amino acid sequence FSSE (SEQ ID NO: 1). A further MD2-antagonist is the peptide MD2-I. Slivka et al., Chembiochem. 10(4): 645-649 (2009).

Candidate MD2 antagonists may be tested in animal models. For example, the animal model can be one for the study of inflammation. The study of inflammation in animal models (for instance, mice) is a commonly accepted practice. For instance, Chen et al. discuss differences between humans and murine models for evaluating sepsis. Chen et al., Surg Clin North Am. 94(6):1135-49 (2014). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the inflammation.

Candidate agents can also be evaluated by directly testing their effectiveness as MD2-antagonist. For example, an ELISA can be used to characterize binding to MD2. Other suitable methods for characterizing MD2 antagonist activity are further described in the examples provided herein.

The methods of the present invention can be used to provide prophylactic and/or therapeutic treatment. MD2-antagonists can, for example, be administered prophylactically to a subject in advance of the occurrence of the development of HMGB1-mediated inflammation. Prophylactic (i.e., preventive) administration is effective to decrease the likelihood of the subsequent occurrence of HMGB1-mediated inflammation in a subject, or decrease the severity of HMGB1-mediated inflammation that subsequently occurs. Prophylactic treatment may be provided to a subject that is at elevated risk of developing HMGB1-mediated inflammation, such as a subject with a family history of HMGB1-mediated inflammation.

Alternatively, the compounds of the invention can be administered therapeutically to a subject that is already afflicted by HMGB1-mediated inflammation. In such methods, the MD2-antagonist is administered after the onset of inflammation or infection. In one embodiment of therapeutic administration, administration of the compounds is effective to eliminate the HMGB1-mediated inflammation; in another embodiment, administration of the compounds is effective to decrease the severity of the HMGB1-mediated inflammation or lengthen the lifespan of the subject so afflicted.

The methods of the invention include administering an MD2-antagonist to a subject in need thereof. The subject is preferably a mammal, such as a domesticated farm animal (e.g., cow, horse, pig) or pet (e.g., dog, cat). More preferably, the subject is a human. A subject can be characterized as being in need if they appear to be suffering from HMGB1- mediated inflammation. In some embodiments, the subject appears to have HMGB1-mediated inflammation as the result of a diagnosis.

When treating HMGB1-mediated inflammation by administering an MD2-antagonist, it can also be useful to administer one or more additional compounds to treat the inflammation or cause of inflammation. For example, when treating inflammation due to infection, antimicrobial agents such as antiviral or antibacterial agents can be co-administered to the subject.

In some embodiments, an antiviral agent is also administered to the subject. The choice of antiviral agent will vary depending on the specific virus and the severity of the patient's condition. Examples of antiviral agents include abacavir, acyclovir, adefovir, amantadine, amprenavir, ampligen, arbidol, atazanavir, atripla, balavir, boceprevirertet, cidofovir, combivir, dolutegravir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon types I-III, lamivudine, lopinavir, loviride, maraviroc, moroxydine, methisazone, nelfinavir, nevirapine, nexavir, oseltamivir (Tamiflu), peginterferon α-2a, penciclovir, peramivir, PF-429242, pleconaril, podophyllotoxin, raltegravir, ribavirin, rimantadine, ritonavir, pyramidine, saquinavir, sofosbuvir, stavudine, tea tree oil, telaprevir, tenofovir, tenofovir disoproxil, tipranavir, trifluridine, trizivir, tromantadine, truvada, traporved, valaciclovir (Valtrex), valganciclovir, vicriviroc, vidarabine, viramidine, zalcitabine, zanamivir (Relenza), and zidovudine.

In some embodiments, an antibacterial agent can be co-administered to the subject. The choice of antibacterial agent will vary depending on the specific bacteria and the severity of the patient's condition. Examples of antibacterial agents include antibacterial agents, such as quinolones, e.g., ciprofloxacin, ofloxacin, moxifloxacin, methoxyfloxacin, pefloxacin, norfloxacin, sparfloxacin, temafloxacin, levofloxacin, lomefloxacin, and cinoxacin; penicillins, e.g., cloxacillin, benzylpenicillin, and phenylmethoxypenicillin; aminoglycosides, e.g., erythromycin and other macrolides; and antitubercular agents, such as rifampicin and rifapentine.

Administration and Formulation

The one or more compounds (e.g., MD2 antagonist) can be administered as pharmaceutically acceptable salts. Pharmaceutically acceptable salt refers to the relatively non-toxic, inorganic and organic acid addition salts of the compounds. These salts can be prepared in situ during the final isolation and purification of the compound, or by separately reacting a purified compound with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

Pharmaceutical compositions of the invention include an MD2 antagonist together with one or more of a variety of pharmaceutically acceptable carriers for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The MD2 antagonist can be administered as a single dose or in multiple doses. Useful dosages of the MD2 antagonist can be determined by comparing their in vitro activity and their in vivo activity in animal models. Methods for extrapolation of effective dosages in mice, and other animals, to humans are known in the art; for example, see U.S. Pat. No. 4,938,949.

MD2 antagonists are preferably formulated in pharmaceutical compositions and then, in accordance with the methods of the invention, administered to a subject, such as a human patient, in a variety of forms adapted to the chosen route of administration. The formulations include, but are not limited to, those suitable for oral, inhaled, rectal, vaginal, topical, nasal, ophthalmic, or parenteral (including subcutaneous, intramuscular, intraperitoneal, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the MD2 antagonist is such that the dosage level will be effective to produce the desired result in the subject.

Inhaled formulations include those designed for administration from an inhaler device. Compositions for inhalation or insufflation include solutions and suspensions in pharmaceutically acceptable, aqueous or organic solvents, or mixtures thereof, aerosols, and powders. Preferably, the compositions are administered by the oral or nasal respiratory route for local or systemic effect. Compositions in preferably pharmaceutically acceptable solvents may be nebulized by use of inert gases. Solution, suspension, or powder compositions may be administered, preferably orally or nasally, from devices that deliver the formulation in an appropriate manner. Nasal spray formulations include purified aqueous solutions of the active agent with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The MD2 antagonist may also be incorporated into sustained-release preparations and devices.

The present invention is illustrated by the following examples. It is to be understood that the particular examples, materials, amounts, and procedures are to be interpreted broadly in accordance with the scope and spirit of the invention as set forth herein.

EXAMPLES

Example 1: MD2 is Required for Disulfide HMGB1-Dependent TLR4 Signaling

Innate immune receptors for pathogen- and damage-associated molecular patterns (PAMP and DAMP) orchestrate inflammatory responses to infection and injury. Secreted by activated immune cells or passively released by damaged cells, HMGB1 is subjected to redox modification that distinctly influences its extracellular functions. Previously, it was unknown how the TLR4 signalosome distinguished between HMGB1 isoforms. Myeloid differentiation factor 2 (MD2) carries a hydrophobic pocket folded by two anti-parallel β-sheets for binding LPS, and confers molecular specificity for LPS interaction and TLR4 signaling. Meng et al., J Biol Chem 285:8695-8702 (2010). Accordingly, here we reasoned that MD2 may similarly discriminate different HMGB1 isoforms to facilitate TLR4-dependent signaling.

Here we demonstrate that the extracellular TLR4 adaptor MD2 binds specifically to the cytokine-inducing disulfide isoform of HMGB1, to the exclusion of other isoforms. Using MD2 deficient mice, as well as MD2 silencing in macrophages, we show a requirement for HMGB1-dependent TLR4 signaling. By screening HMGB1 peptide libraries, we identified a tetramer (FSSE (SEQ ID NO: 1), designated P5779) as a specific MD2-antagonist preventing MD2/HMGB1 interaction and TLR4 signaling. P5779 does not interfere with LPS-induced cytokine/chemokine production, thus preserving PAMP-mediated TLR4/MD2 responses. Furthermore, P5779 can protect mice against hepatic ischemia/reperfusion injury, chemical toxicity and sepsis. These findings reveal a novel mechanism by which innate systems selectively recognize specific HMGB1 isoforms. The results may direct towards strategies aimed at attenuating DAMP-mediated inflammation while preserving anti-microbial immune responsiveness.

Results and Discussion

Cytokine-Inducing (Disulfide) HMGB1 Effectively Binds to MD2

HMGB1 contains three redox-sensitive cysteine residues that are modified by redox reactions to produce multiple HMGB1 isoforms that extracellularly express or lack chemokine or cytokine activities. To elucidate the underlying molecular mechanisms, we examined whether MD2, an extracellular adaptor receptor of the TLR4 signalosome, can discriminate various HMGB1 isoforms with their distinct inflammatory properties. Different forms of HMGB1, produced by point mutations or chemical modifications by exposure to mercury thiolates or the reducing agent dithiothreitol, were tested for their MD2-binding properties. Consistent with previous reports (Venereau et al., J Exp Med 209:1519-1528 (2012); Yang et al., Mol Med 18:250-259 (2012)), only the disulfide HMGB1 isoform induced TNF secretion (FIG. 1A). Biosensor-based surface plasmon resonance analysis (BIAcore) confirmed that only the disulfide HMGB1 binds to MD2 with high affinity (apparent Kd=12 nM) regardless whether MD2 or HMGB1 was immobilized on the sensor chip (FIG. 1B). In contrast, HMGB1 was incapable of directly binding to TLR4 (FIG. 1B) in the absence of MD2 although TLR4 was functionally active in MD2 binding in BIAcore analysis, implicating MD2 as an essential participant in the HMGB1/TLR4 signaling pathway. Unlike the disulfide isoform of HMGB1, H2S-modified, fully reduced or sulfonyl HMGB1 failed to induce TNF release from macrophage cultures (FIG. 1A), with more than a 1,000-fold reduction in MD2 binding as compared to disulfide HMGB1 (FIG. 1B). Notably, chemical modification of the cysteine 106 of the disulfide HMGB1 also abolished the TNF-stimulating and MD2-binding properties, indicating a critical role of the thiol-cysteine 106 in the regulation of HMGB1 cytokine activity (FIG. 1A-B).

To further study HMGB1-MD2 interactions, immunoprecipitation assays were employed to pull-down MD2 from HMGB1-expressing cell lysates. Co-incubation with calmodulin binding protein (CBP)-tagged disulfide HMGB1, but not CBP tag alone, pulled down MD2 protein from yeast cells transfected with an MD2-expressing construct (FIG. 1C), confirming that MD2 binds disulfide HMGB1. Furthermore, this interaction was blocked by monoclonal anti-HMGB1 antibodies, but not by irrelevant IgG, demonstrating that the HMGB1-MD2 interaction is specific and targetable by antagonists (FIG. 1D).

MD2 is Required for HMGB1-Mediated Inflammatory Responses

Figure 2:
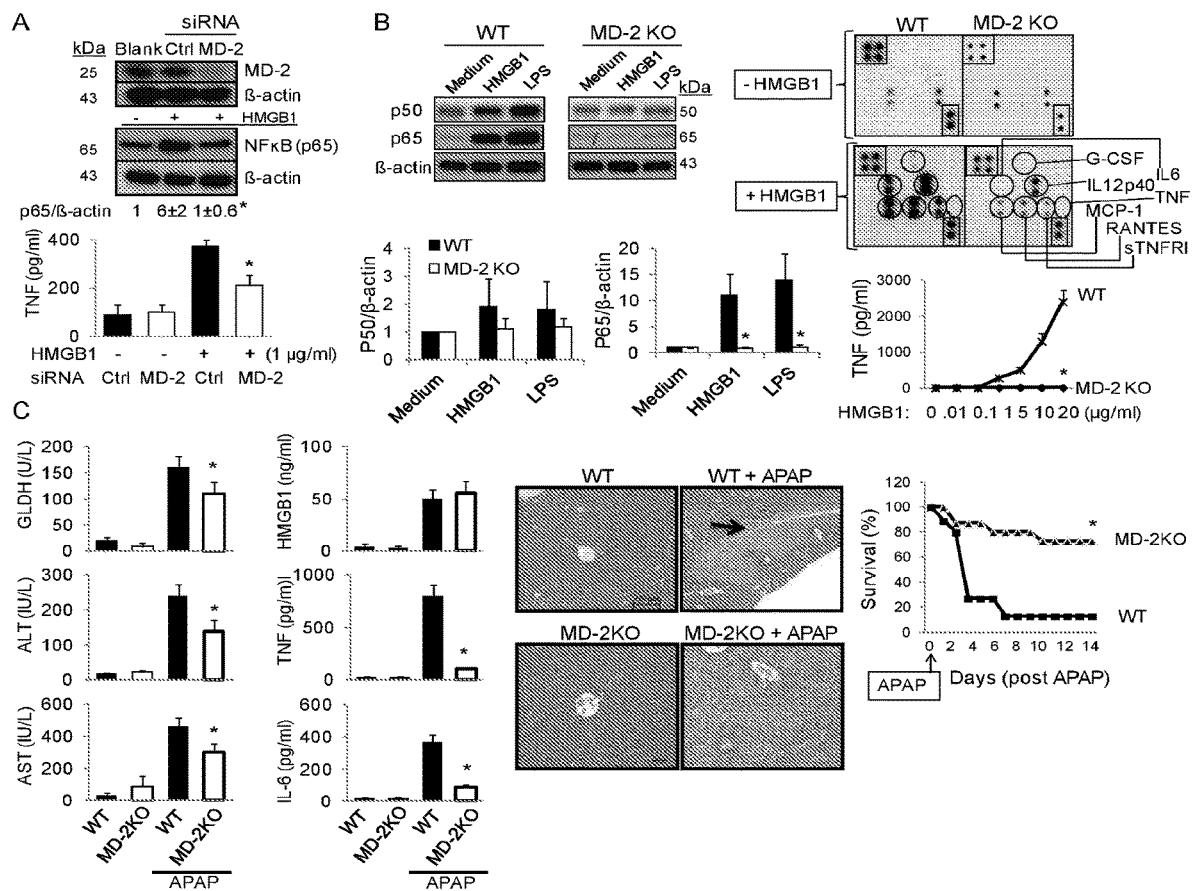
FIGS. 2A-2C provide graphs and images showing MD2 is indispensable for HMGB1-dependent TLR4 signaling. (A) Upper panel: knockdown of MD2 (siRNA) was performed on RAW 264.7 cells. MD2 and NF-κB levels (p65) were assessed by western blotting. The level of NF-κB (p65) protein was normalized relative to level of β-actin (ratio) by densitometry, and expressed as the fold change over un-stimulated cells. Lower panel: HMGB1-induced TNF release from RAW 264.7 cells with MD2 knockdown (open bars) or control siRNA (solid bars). *: P<0.05 vs. control siRNA group. N=4-5 experiments. (B) Left panel:HMGB1 (2 μg/ml) or ultrapure LPS (200 ng/ml) were used to stimulate primary peritoneal macrophages from wild type (WT) or MD2 KO mice for 16 hours, and NF-κB (p50 and p65) protein levels in nuclear extracts were assessed by western blotting (upper left panels). NF-κB activation is expressed as of p50 or p65 relative to β-actin and calculated as the fold change over un-stimulated cells (lower left graphs). Right panel: Mouse macrophages were stimulated with HMGB1 and cytokine released was measured using mouse cytokine Ab array (G-CSF, IL-12p40, IL-6, TNF, RANTES, MCP-1, sTNFR1; upper right panel) or ELISA (for TNF, lower right graph). *: P<0.05 vs. WT group. N=5 separate experiments. (C) WT or MD2 KO mice were challenged with APAP in a liver injury model, and were euthanized 24 h later to measure serum levels of liver enzymes (GLDH, ALT, and AST; left column graphs) and cytokines (HMGB1, TNF and IL-6; right column graphs). *: P<0.05 vs. WT APAP group. N=5-13 mice per group. Representative H&E staining of liver tissues from these mice are shown. N=5-8 mice per group (magnification, ×200; the arrow indicates necrosis region; middle panel). Scale bar=100 μm. Animal survival after receiving lethal dose of APAP in WT and MD2 KO mice was assessed (percent survival). N=15 mice per group. *: P<0.05 vs. wild type (right panel graph).

To further assess the importance of MD2 in HMGB1-mediated cytokine induction, we used siRNA to knockdown MD2 expression in murine macrophage-like RAW 264.7 cells or human (THP-1) monocytes. The silencing of MD2 expression (by 80-90%) was accompanied by a significant reduction of HMGB1-stimulated NF-κB activation and TNF release in both murine macrophages and human monocytes (FIG. 2A). To confirm the requirement for MD2 in HMGB1-induced innate immune activation, thioglycollate-elicited peritoneal macrophages were isolated from wild type and MD2 knockout (KO) mice, and stimulated by disulfide HMGB1. Disruption of MD2 expression resulted in complete impairment of both LPS- and HMGB1-induced activation of NF-κB, secretion of cytokines (TNF and IL-6) and chemokines (e.g., RANTES and MCP-1) (FIG. 2B). The release of IL-12/p40 stimulated with HMGB1 is via an MD2 independent mechanism, likely attributable to signaling via other receptors.

Figure 3:
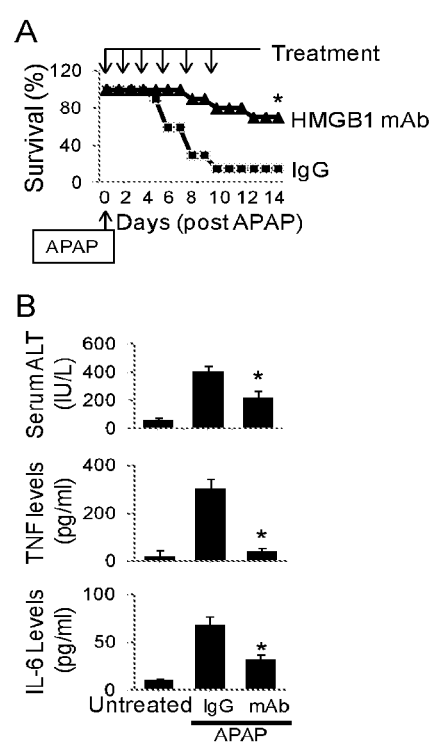
FIGS. 3A and 3B provide graphs showing monoclonal anti-HMGB1 antibody administration ameliorates APAP-induced liver injury in mice. (A) Mice received an APAP injection (i.p.) followed by treatment with an anti-HMGB1 antibody or control IgG injection (i.p., see Methods). Animal survival (% survival) was assessed. N=20 mice/group. *: P<0.05 vs. IgG group. (B) Serum levels of liver enzyme (ALT) and cytokines (TNF and IL-6) at 24 h post-APAP were measured in mice receiving treatment of anti-HMGB1 Ab or control IgG (see Methods). N=10 mice/group. *: P<0.05 vs. IgG group.

HMGB1 is an important mediator of acetaminophen (APAP)-induced hepatotoxicity. Antoine et al., J Hepatol 56:1070-1079 (2012). To evaluate the in vivo importance of MD2 in HMGB1-induced inflammatory responses, we studied the impact of MD2 deficiency on sterile inflammation using the APAP intoxication model. The disruption of MD2 expression resulted in a significant reduction in acute hepatic injury, as assessed by liver enzyme release (GLDH, AST and ALT) and histological analysis of liver necrotic lesions compared to wild type (WT) mice subjected to APAP injection (FIG. 2C, arrow). Furthermore, the lessened hepatic damage in MD2 KO mice was accompanied by significant reduction in cytokine (TNF and IL-6) release and APAP-induced animal lethality, confirming an essential role for MD2 in sterile inflammation and injury (FIG. 2C). Notably, serum HMGB1 levels were comparably elevated in wild type and MD2 KO mice at 24 hour post APAP administration (FIG. 2C). The central role of HMGB1 in APAP-induced liver toxicity was further confirmed by using a HMGB1-neutralizing monoclonal antibody, which significantly inhibited APAP-induced release of hepatic enzymes (ALT) and pro-inflammatory cytokines (TNF and IL-6), and improved survival (FIG. 3). Taken together, these in vivo experimental data reveal an essential role for MD2 and HMGB1 in the pathogenesis of sterile injury.

Development of a Novel MD2-Binding Peptide as an HMGB1-Specific Inhibitor

Figure 4:
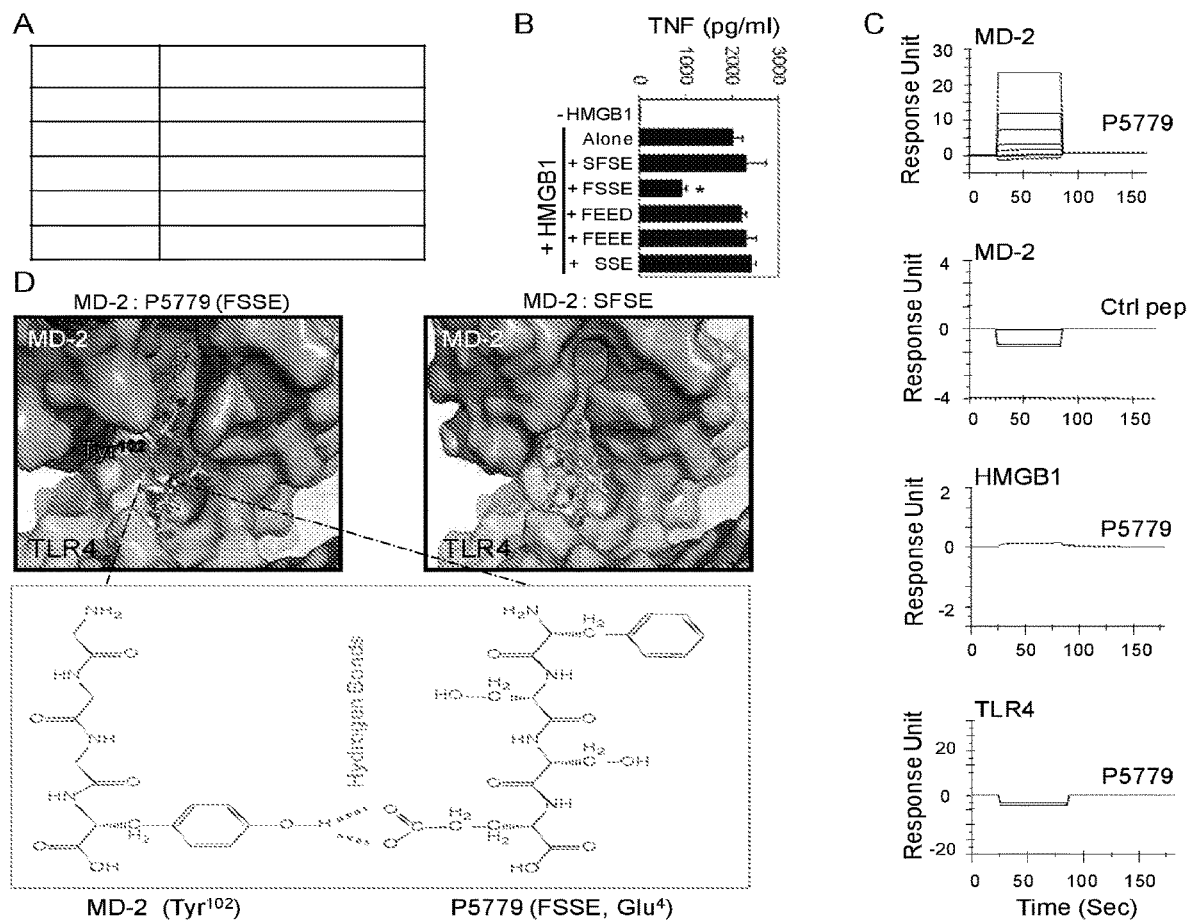
FIGS. 4A-4D provide graphs and images showing the results of screening for HMGB1 inhibitors. (A) SPR analysis was performed to test the interaction of MD2 (coated on the chip) with P5779 (FSSE) (SEQ ID NO: 1) and other peptides (100 nM). Kd values are shown. Data are representative of 3 experiments. (B) Primary human macrophages were stimulated in vitro with HMGB1 (1 μg/ml) plus different peptides (50 μg/ml) for 16 h, and TNF release was measured by ELISA. N=4-5 experiments. *: P<0.05 vs. HMGB1 alone. (C) SPR analysis was performed to measure binding of P5779 (12.5, 25, 50 and 100 nM), or scrambled control (ctrl) peptide (100 nM), to human MD2 (Kd=0.65 μM for P5779), HMGB1 or TLR4 (coated on the chip). Data are representative of three experiments. (D) Schematic illustration showing molecular docking of MD2 with tetramer peptides FSSE (SEQ ID NO: 1) (left) and SFSE (SEQ ID NO: 5) (right). The brown area represents the surface of the peptide binding pocket of MD2 and the green area denotes the TLR4 protein surface. The lower panel shows hydrogen bonds and van der Waals interactions. P5779, with a stronger van der waals interaction than control is fully extended into the hydrophobic pocket of MD2 and forms an additional hydrogen bond with Tyr102 of MD2.

Having identified a critical involvement of the cysteine 106 region of HMGB1 in HMGB1/MD2 interaction and HMGB1/TLR4 signaling, we utilized a rational strategy to screen for mimetic peptide inhibitors. A series of trimer and tetramer peptides spanning the cysteine 106 region and incorporating cysteine homologs were screened for MD2 binding properties using the BIAcore technology and molecular docking technique (FIG. 4A,C-D). Although most peptides lacked MD2-binding capacity, we identified one epitope within the HMGB1 B box domain that acted as a potent HMGB1-specific inhibitor. Molecular docking simulation revealed that the FSSE (SEQ ID NO: 1) (P5779) tetramer fully extended into the hydrophobic pocket of MD2, thereby forming maximal van der Waals interaction with surrounding hydrophobic residues along with an additional hydrogen bond with the Tyr102 (FIG. 4D). Consequently, it bound to MD2 with a Kd value of 0.65 μM and significantly inhibited HMGB1-induced TNF release from human macrophages (FIG. 4A-B). This interaction was specific, as P5779 failed to bind to other proteins such as HMGB1 and TLR4 in the absence of MD2 (FIG. 4C). Similarly, scrambling the amino acid sequence of P5779 (control peptide) abolished the MD2-binding capacity in BIAcore experiments (FIG. 4C) and in molecular docking analysis (FIG. 4D).

Figure 5:
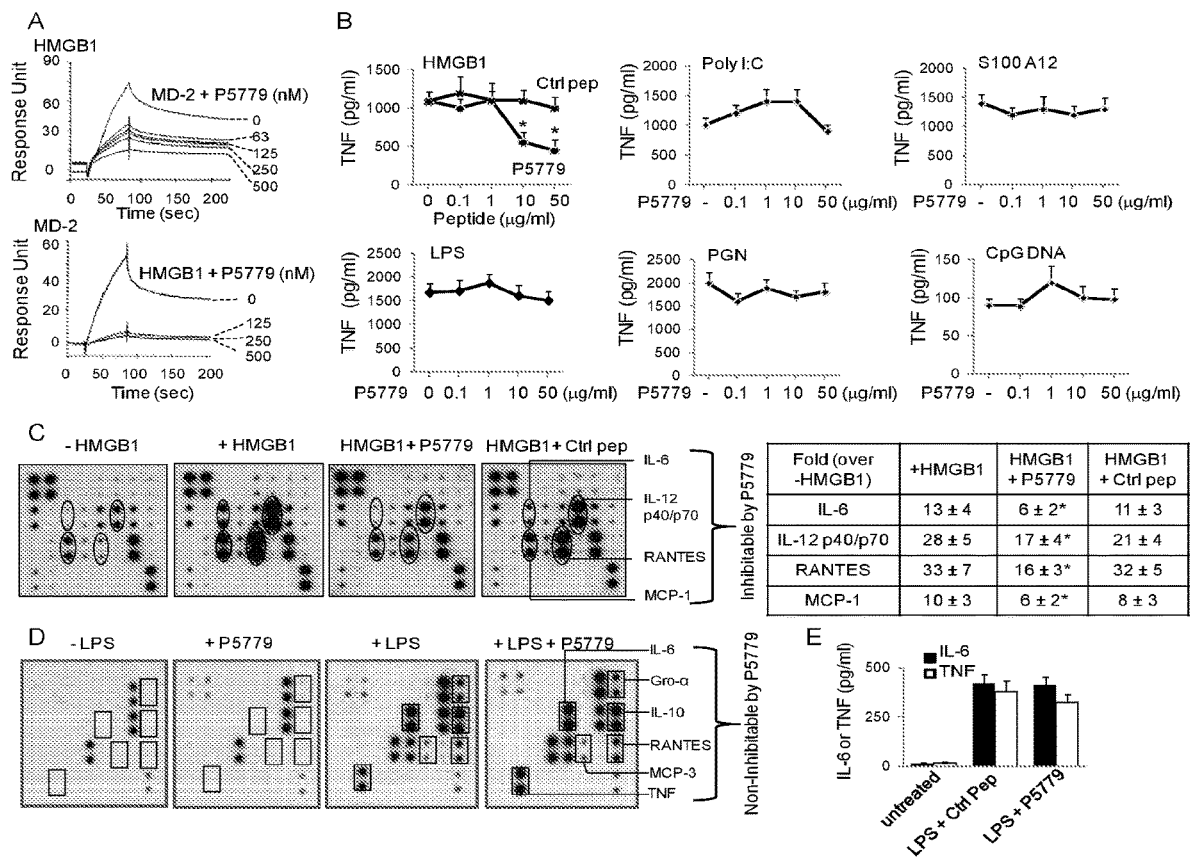
FIGS. 5A-5E provides graphs and images showing the development of a tetramer peptide (P5779) as an MD2-binding HMGB1-specific inhibitor. (A) On SPR analysis, HMGB1 was coated on the chip and MD2 (1 μM) was flowed over as analyte, plus different amounts of P5779 as shown. Inhibition of HMGB1 binding to MD2 by P5779 ($IC_{50}$=29 nM) was assessed (upper graph). In the reverse experiment, human MD2 was coated on the chip and HMGB1 (1 μM) plus different amounts of P5779 were added as analytes. HMGB1 binding to MD2 was inhibited by P5779 ($IC_{50}$=2 nM) (lower graph). Data are representative from 3 separate experiments. (B) Human primary macrophages, isolated from human blood, were stimulated with HMGB1 (1 µg/ml), or other stimuli (Poly I:C, S100A12, LPS, PGN and CpGDNA) in vitro, plus increasing amounts of P5779 (or scrambled control peptide) for 16 hours. TNF released was measured by ELISA. N=4-5 experiments. *: $P<0.05$ vs. HMGB1 plus control peptide (ctrl). (C) Thioglycollate-elicited peritoneal mouse macrophages were stimulated in vitro with HMGB1 (1 µg/ml) plus P5779 or control peptide (ctrl, 50 µg/ml) for 16 h, and extracellular levels of various cytokines were analyzed by mouse Cytokine Ab Array (left panels). Data are representative of 3-4 experiments, each performed in duplicate and expressed as fold increase over unstimulated cells using densitometry (–HMGB1) (right table). *: $P<0.05$ vs. +HMGB1 group. (D) Primary human macrophages, isolated from blood, were stimulated in vitro with LPS (2 ng/ml) for 16 h in the absence or presence of P5779 (50 µg/ml) or control peptide (ctrl), and extracellular levels of various cytokines were analyzed by human cytokine Ab array (left panels). Data are representative of 3 repeats. (E) Male C57BL/6 mice received an LPS injection (8 mg/kg, i.p.) plus P5779 or control peptide (ctrl) (500 µg/mouse, i.p.). Animals were euthanized 90 minutes later. Serum TNF and IL-6 levels were measured by ELISAs. N=5 mice per group.

To evaluate the therapeutic potential of the MD2-binding peptide, we next studied whether P5779 was capable of disrupting MD2/HMGB1 interactions, thereby inhibiting HMGB1-induced cytokine production. P5779 inhibited the MD2/HMGB1 interaction in a concentration-dependent manner when either MD2 or HMGB1 was coated onto the BIAcore sensor chip (FIG. 5A). Furthermore, P5779 inhibited HMGB1-induced TNF release in primary human macrophages in a concentration-dependent fashion (FIG. 5B). The effective concentration of P5779 that suppressed 50% TNF release (IC50) was approximately 5 μg/ml in the presence of HMGB1 at 1 μg/ml. Scrambling the amino acid sequence of P5779 abolished the capacity to inhibit HMGB1-induced TNF release (FIG. 5B). Exposure of macrophages to P5779 failed to inhibit TNF release mediated by Poly I:C, S100A12, LPS, PGN and CpG DNA (FIG. 5B). P5779 also significantly reduced HMGB1-induced release of other cytokines including IL-6 and IL-12p40/p70 and chemokines such as RANTES and MCP-1 (FIG. 5C). P5779 did not inhibit LPS-stimulated cytokine/chemokine release in vitro in macrophages (FIG. 5D), and failed to attenuate LPS-induced systemic cytokine levels in vivo, even when administered at high doses (8 mg/kg) in mice (FIG. 5E). Thus, P5779 selectively attenuates HMGB1-MD2-TLR4 signaling without inhibiting macrophages activation in response to PAMPs.

Figure 6:
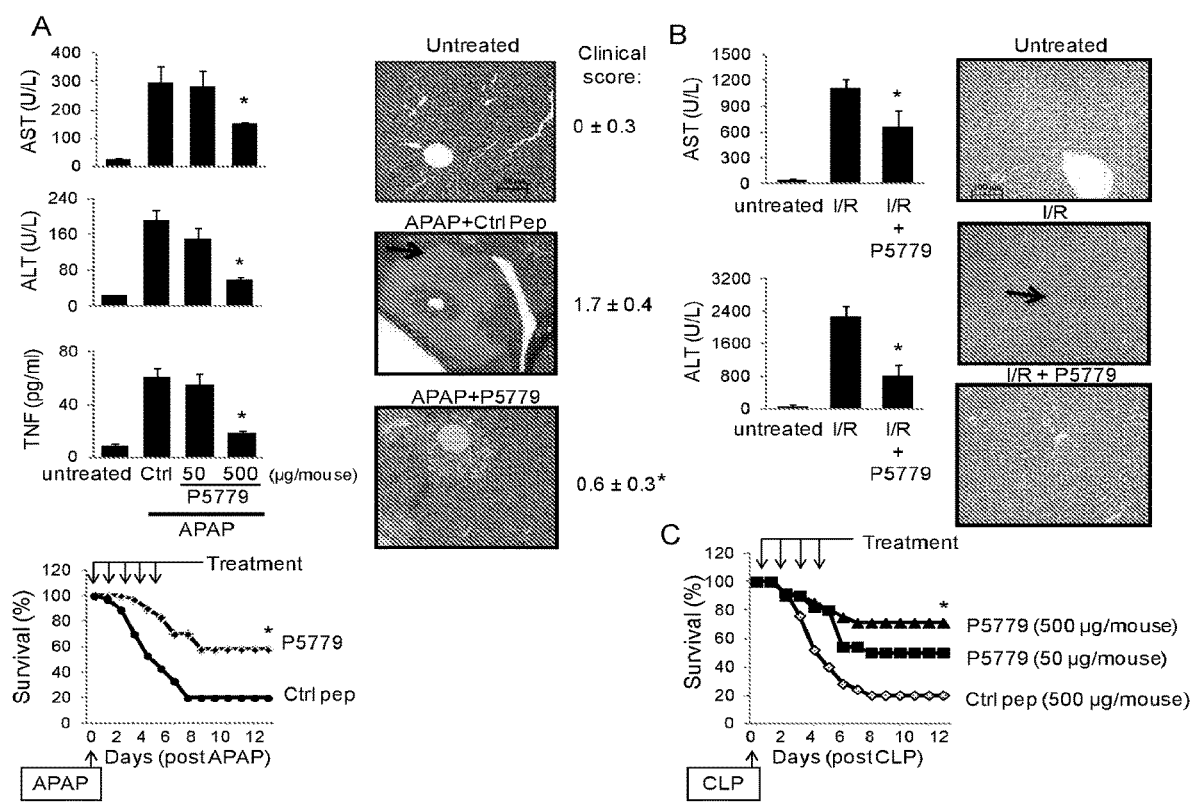
FIGS. 6A-6C provide graphs and images showing treatment with the HMGB1 inhibitor, P5779, ameliorates APAP-mediated toxicity, ischemia/reperfusion injury and sepsis mortality in vivo. (A) C57BL/6 mice received an APAP injection (i.p. Methods) and were administered with P5779 (at doses indicated) or control peptide (ctrl, 500 µg/mouse; i.p.). Mice were euthanized at 24 h post-APAP and serum enzyme levels (ASL and ALT) and cytokine levels (TNF) were measured by ELISAs (left upper graphs). N=6-10 mice per group. In survival experiments, mice received an APAP injection (i.p.) and were administered with P5779 or control peptide (ctrl, i.p. see Methods). Survival was monitored for 2 weeks (percent survival). N=30 mice/group (left lower graph). Right Panels: Representative H&E images of liver tissue sections are shown for normal (untreated) or APAP-injected mice receiving P5779 or control peptides. Clinical scores were assessed and shown on the right. Liver necrosis is demonstrated by arrows (magnification, ×200). Scale bar=100 µm. N=6-10 mice/group. *: $P<0.05$ vs. control peptide group. (B) P5779 or control peptide was administered (500 µg/mouse, i.p.) at the time of ischemia/reperfusion (I/R) surgery and mice were euthanized 6 h later to measure serum levels of ALT and AST (left column graphs), and to evaluate histological liver injury. *: $P<0.05$ vs. I/R group. N=5-7 mice/group. Representative H&E liver tissue sections are shown (right panels, neutrophil infiltration: arrow; magnification, ×200). Scale bar=100 µm. N=3-5 mice per group. (C) Mice received CLP surgery, and P5779 or control peptide (Ctrl) was administered i.p. at the doses indicated. Animal survival was monitored for 2 weeks (% survival). N=20 mice/group. *: $P<0.05$ vs. control peptide group.

Therapeutic Efficacy of MD2-Targeted P5779 in Acetaminophen (APAP) Toxicity, Ischemia and Sepsis In the APAP-induced liver toxicity model, P5779 treatment dose-dependently reduced APAP-induced elevation of hepatic serum enzymes (AST, ALT), pro-inflammatory cytokines (TNF), liver necrosis and improved survival (FIG. 6A, arrow). In sterile injury mediated by hepatic ischemia/reperfusion (I/R), P5779 also significantly blunted hepatic serum enzyme release (AST, ALT) and neutrophil infiltration (FIG. 6B, arrow). In addition, treatment with P5779 in a sepsis model induced by cecal ligation and puncture (CLP) significantly and dose-dependently improved survival rates as compared to scrambled peptide-treated controls (FIG. 6C). Importantly, P5779 was effective even when administered 24 hours after onset of the peritonitis, consistent with the known delayed pathogenic role of HMGB1 in sepsis sequelae. Taken together, these results indicate that P5779 disrupts binding of disulfide HMGB1 to MD2 thereby attenuating HMGB1-mediated organ failure and mortality in vivo.

These results reveal a novel mechanism of selective innate immune cell recognition of HMGB1 by MD2 that discriminates the HMGB1 isoforms. By screening HMGB1 peptide libraries, we identified a novel tetramer peptide (FSSE (SEQ ID NO:1), P5779) that specifically prevents the MD2-HMGB1 interaction without impairing the MD2/LPS/TLR4 signaling in innate immune cells. This peptide conferred protection not only in animal models of sterile injury-elicited inflammatory diseases but also following a lethal infection challenge, opening the possibility of developing novel therapeutic strategies to attenuate DAMP-mediated injurious inflammatory responses without inhibiting PAMP-elicited innate immunity.

MD2 carries a β-cup fold structure composed of two anti-parallel β-sheets that form a large hydrophobic pocket for binding to LPS. The estimated affinity of MD2 binding to HMGB1 (12 nM) is comparable to MD2 binding to LPS (65 nM) (Visintin et al., J Immunol., 175(10):6465-72 2005). Further structural analysis is required to reveal the disulfide HMGB1 binding site on MD2.

HMGB1-neutralizing antibodies are protective against sterile injury (Tsung et al., J Exp Med 201:1135-1143, 2005), and agents capable of inhibiting HMGB1 release or its extracellular activities (Wang et al., Science 285:248-251

(1999)) also confer protection against sepsis. During early stages of sepsis, PAMP-mediated inflammatory responses are essential to host defense. At later stages, the release of DAMPs amplifies the cytokine storm and organ dysfunction. Wang et al., Expert Opin Ther Targets 18:257-268 (2014). This notion is supported by recent observations that HMGB1 levels are persistently elevated during later stages of sepsis, despite termination of the initial infection, and contribute to long-term pathological consequences of sepsis. Valdes-Ferrer et al., Shock 40:492-495 (2013). Microbial-induced sepsis can be clinically indistinguishable from the sterile injury-elicited systemic inflammatory response syndrome (SIRS). Sursal et al., Shock 39:55-62 (2013). Based on the findings that TLR4/MD2 acts as a mutually exclusive signaling receptor complex for disulfide HMGB1, it is possible to develop strategies that selectively attenuate DAMP-mediated inflammatory responses while preserving PAMP-mediated signaling.

Substantial evidence supports the necessity to preserve early PAMP-mediated innate immune responses to counteract microbial infections. For instance, defective TLR4 signaling in C3H/HeJ mice is associated with aggravated disease severity and increased mortality in animal models of infection. Khanolkar et al., J Virol 83:8946-8956 (2009). LPS enhances macrophage phagocytic activity through TLR4 and selective deletion of TLR4 on myeloid cells impairs bacterial clearance in the CLP model. Deng et al., J Immunol 190:5152-5160 (2013). These findings emphasize the importance of generating therapeutic approaches to selectively target damage-mediated inflammation while preserving physiological protective immune responses. The discovery of P5779 as an MD2-targeting selective inhibitor for the DAMP-, but not the PAMP-elicited inflammatory responses provides such a novel therapeutic tool.

Materials and Methods

Reagents. Human TLR4/MD2 complex, human MD2, TLR2, soluble RAGE were obtained from R & D system Inc., (Minneapolis, Minn.). Lipopolysaccharide (LPS, *E. coli.* 0111:B4), acetaminophen, triton X-114, peptidoglycan from *Bacillus subtili*, blasticidin S., NaSH, mouse IgG, human macrophage-colony stimulating factor (M-CSF) were purchased from Sigma (St. Louis, Mo.). Protein A/G agarose and isopropyl-D-thiogalactopyranoside (IPTG) were from Pierce (Rockford, Ill.). NHS-activated sepharose 4 fast flow beads were obtained from GE Healthcare (Cat #17-0906-01, Uppsala, Sweden). Thioglycollate medium was purchased from Becton Dickinson Co., (Sparks, Md.). Ultra pure LPS (Cat # tlrl-pelps), polyinosinic-polycytidylic acid (poly I:C) and type B CpG oligo-nucleotide were obtained from InVivogen (San Diego, Calif.). Human S100 A12 was from Circulex Co. (Bangkok, Thailand). Anti-human and mouse MD2 antibodies were obtained from Imgenex (San Diego, Calif.). Anti-CBP tag antibody was from GenScript (Piscataway, N.J.). Anti-p50 antibody (E381) and anti-p65 antibody (sc-372) were obtained from Epitomics (Burlingame, Calif.) and Santa Cruz Biotech (Dallas, Tex.), respectively. Serum ALT and AST levels were determined by color endpoint assay kits from BIOO Scientific (Austin, Tex.).

Preparations of HMGB1 proteins, antibodies and peptides. Recombinant HMGB1 was expressed in *E. coli* and purified to homogeneity as described previously. Li et al., J Immunol Methods 289:211-223 (2004). This cytokine-stimulating HMGB1 contains a disulfide bond between cysteines 23 and 45, and reduced thiol on cysteine 106, characterized by liquid chromatography tandem mass spectrometric analysis (LC-MS/MS). Yang et al., Mol Med 18:250-259 (2012). HMGB1 with redox modifications was created chemically by a synthetic formation of mercury thiolate on cysteine at position 106 (Hg-HMGB1), by S-sulfhydration (H2S) to convert cysteine thiol (—SH) group to —SSH or by mutation of cysteine 106 to alanine (C106A HMGB1) as described previously. Yang et al., Proc Natl Acad Sci USA 107:11942-11947 (2010). HMGB1 with cysteine modified by H2S was generated by incubating HMGB1 with NaSH (5 mM) for 3 hours at room temperature. Oxidized or DTT-reduced HMGB1 was prepared as previously described (Yang et al., 2012). The LPS content in HMGB1 was measured by the Chromogenic Limulus Amebocyte Lysate Assay (Lonza, Walkersville, Md.). HMGB1 was extracted with triton X-114 to remove any contaminating LPS as described previously (Li et al., 2004). The purity and integrity of all recombinant proteins were verified by Coomassie Blue staining after SDS-PAGE, with a purity predominantly above 85%. The LPS content in all HMGB1 protein preparations is non-detectable or less than 10 pg/mg protein as measured by Limulus assay. Monoclonal anti-HMGB1 antibody (2g7) was generated as reported previously. Qin et al., J Exp Med 203:1637-1642 (2006). Trimer or tetramer peptides (FSSE (SEQ ID NO: 1), FSSEY (SEQ ID NO: 21, FEEE (SEQ ID NO: 3), FEED (SEQ ID NO: 4), SSE, SFSE (SEQ ID NO: 5)) and calmodulin binding peptide (CBP) were all customer-made from GeneMed Inc., (San Antonio, Tex.). The peptides were purified to 90% purity as determined by HPLC. Endotoxin was not detectable in the synthetic peptide preparations as measured by Limulus assay. The peptides were first dissolved in DMSO and further diluted in PBS as instructed by the manufacturer, and prepared freshly before use. Pre-casted mini-protean Tris-Tricine gels were from BioRad Lab (Hercules, Calif.).

Cell isolation and culture. Thioglycollate-ellicited peritoneal macrophages were obtained from mice (C57BL/6 or gene knock out, male, 10-12 weeks old) injected with 2 ml of sterile 4% thioglycollate broth intraperitoneally as previously described (Yang et al., 2010). Murine macrophage-like RAW 264.7 (TIB-71) and human leukemia monocytes THP-1 (TIB-202) were obtained from American Type Culture Collection (ATCC, Rockville, Md.). Human primary monocytes were purified by density gradient centrifugation through Ficoll from blood donated by normal individuals as reported before (Yang et al., 2010). Human primary macrophages in 96 well plate were stimulated with HMGB1 (1 µg/ml), TLR4 agonist LPS at 4 ng/ml, TLR3 agonist poly I:C at 50 µg/ml and TLR2 agonist peptidoglycan (PGN) at 5 µg/ml, RAGE agonist S100A12 at 50 µg/ml and TLR9 agonist CpG-DNA at 1 µM, plus increasing amounts of P5779 (or scrambled control peptide) as indicated for 16 hours. TNF released was measured by ELISA.

Immuno-precipitation assay. Recombinant rat HMGB1 with a calmodulin binding protein (CBP) tag, or CBP peptide alone (10 µg), was incubated overnight with human MD2 supernatant (50 pre-cleared with calmodulin beads) at 4° C. with gentle shaking. Human MD2 supernatant was obtained from sf9 insect cells transfected with human MD2. Teghanemt et al., J.B.C., 283:21881-21889 (2008). Both HMGB1 and MD2 supernatant contained non-detectable amounts of LPS as measured by Limulus amebocyte lysate assay. The mixture of CBP-HMGB1, or CBP and MD2 was then incubated with calmodulin beads (30 µl drained beads) for 1 hour at 4° C. After extensive washing with PBS containing 0.1% triton X100, proteins bound to the beads were analyzed by Western blot probed with anti-human MD2 or anti-CBP antibodies.

Cytokine and NF-κB measurements. Levels of TNF and IL-6 released in the cell culture or from mice serum were measured by ELISA kits (R & D System Inc., Minneapolis, Minn.). Serum HMGB1 levels were measured by ELISA kit (IBL international, Hamberg, Germany). Cytokine expression profile from thioglycollate-elicited peritoneal macrophages of mice or primary human macrophages was determined by mouse or human cytokine array C1 (Raybiotech, Norcross, Ga.) according to manufacturer's instructions. Twenty two cytokines or chemokines were determined simultaneously. NF-κB activation was analyzed by detecting p50 and p65 expression in the nuclear fraction by western blot. β-actin expression was also measured as control for equal loading of samples. Western blots were scanned with a silver image scanner (Silver-scanner II, Lacie Limited, Beaverton, Oreg.), and the relative band intensity was quantified using ImageJ software (v1.59, National Institute of Health) and is expressed as a ratio to the amount of β-actin.

Surface plasmon resonance analysis. Biacore T200 instrument was used for real-time binding interaction studies. For HMGB1-MD2 binding analyses, human MD2 was immobilized onto a CMS series chip (GE Life Sciences). One flow-cell was used as a reference and thus immediately blocked upon activation by 1 M ethanolamine (pH 8.5). The sample flow-cell was injected with disulfide HMGB1 (or isoforms) (in 10 mM acetate buffer, pH 5.2) at a flow rate of 10 μL/min for 7 min at 25 C. Increasing concentrations of disulfide HMGB1 or isoforms of HMGB1 (C106A, sulfonyl, fully reduced, Hg or $H_2$S-modified HMGB1, at 1 μM) were flowed over immobilized MD2. In reverse fashion, HMGB1 was coated on the chip and various amounts of MD2 were added as analyte. Findings were confirmed by using two additional human MD2 proteins from Dr. D. Golenbock (Worcester, Mass.) and Dr. Timothy Billiar (Pittsburgh, Pa.). For TLR4-HMGB1 binding experiment, human TLR4 was coated on the chip and disulfide HMGB1 (100 nM) was added as analyte. For peptide screening experiments, human MD2 was coated on the sensor chip, and various small peptides (FSSE (SEQ ID NO: 1), FSSEY (SEQ ID NO: 2), FEEE (SEQ ID NO: 3), FEED (SEQ ID NO: 4), SSE, SFSE (SEQ ID NO: 5), 100 nM) were added as analytes. The dissociation time was set for two minutes, followed by a one-minute regeneration using a 10 mM NaOH solution. The Kd was evaluated using the BIAcore evaluation software. For experiments using HMGB1 antibody to block MD2-HMGB1 interaction, human MD2 was coated on the chip, HMGB1 was added as analyte (100 nM) plus increasing amounts of HMGB1 mAb or control IgG and response units were recorded.

Molecular docking of MD2 with peptides. The crystal structure of the MD2/TLR4 was obtained from the Protein Data Base (PDB, code: 3VQ2), and molecular docking was performed by using the MOE software as previously described. Zan et al., Mol Sim 6, 498-508 (2012). A molecular visualization system, the Pymol 0.99, was used to construct the 3-dimensional figures.

Knockdown MD2 in RAW 264.7 and THP-1 cells using siRNA. For MD2 knockdown in RAW 264.7 cells, cells were transfected with mouse MD2 or control siRNA (50 nM, on-target plus smart pool, Dharmacon, Lafayett, Colo.) using DharmaFect1 transfection reagent. To knockdown MD2 in THP-1 cell, transfection with MD2 specific siRNA was performed by using Amaxa Nucleofector kit. The efficiency of knockdown was confirmed by western blot probed with anti-MD2 antibody at 48 hours after transfection. At 48 hours post-transfection, cells were stimulated with HMGB1 (1 μg/ml) for 16 hours. Cell lysate and supernatant were collected and analyzed by western blot or ELISA. NF-κB measurements on RAW 264.7, THP-1 or primary mouse macrophages from MD2 knockout mice were performed using NE-PER Protein Extraction Kit (Thermo Scientific, Hudson, N.H.).

Animals. Male C57BL/6 mice were obtained from Jackson Laboratory (Bar Harbor, Me.). MD2 knockout (on C57BL/6 background) mice were purchased from Riken Bio-Resource Center (Ibaraki, Japan). All animals were maintained at The Feinstein Institute for Medical Research or University of Pittsburgh under standard temperature and light cycles, and all animal procedures were approved by the institutional animal care and use committee.

For genotyping of MD2 KO mice from tail snips, PCR primers were designed by Riken Bio-Resource Center and were obtained from Invitrogen Inc., (Carlsbad, Calif.). Same primers were used to identify wild type (PCR product=2,000 bp) and MD2 knockout (PCR product=800 bp) in genotyping.

For murine hepatic warm ischemia/reperfusion (I/R), a 70% warm liver I/R Model was performed as previously described. Tsung et al., J Exp Med 201:1135-1143 (2005). Mice received intraperitoneal injection of P5779 (500 μg/mouse) or vehicle at the time of surgery and were euthanized at six hours afterwards. Whole blood was collected by cardiac puncture, and liver was harvested and fixed in 10% formalin for analysis.

For cecal ligation and puncture (CLP), C57BL/6 mice (male, 8-12 weeks of age) were subjected to CLP procedure as described before (Yang et al., 2004). P5779 or scrambled control peptide were administered intraperitoneally at 50 or 500 μg/mouse, treatment was given once a day for 4 days starting at 24 hours after CLP surgery. Survival was monitored for 2 weeks.

For the acetaminophen (APAP) hepatic toxicity model, three sets of experiments were conducted. In all experiments, mice were routinely fasted overnight and received intraperitoneal (IP) injection of APAP (350 mg/kg for survival studies and 400 mg/kg for serum measurements when mice were euthanized at 24 h post-APAP) as previous described. Antoine et al., J Hepatol 56:1070-1079 (2012) The first set of experiments was performed using male MD2 KO or C57/BL6 mice (8-12 weeks old). Mice had APAP injection and were euthanized 24 hours later (for serum measurements) or monitored for 2 weeks (for survival studies). The second set of experiments was performed using anti-HMGB1 antibody in APAP model in wild type male (C57/BL6) mice. In survival experiments, mice had APAP injection and received anti-HMGB1 antibodies (5 μg/mouse, IP, once daily for 4 days followed by two additional doses once every other day beginning at 2 hours post-APAP). Irrelevant non-immune IgG was used as controls. For serum measurements, mice subjected to APAP injection and received injection of monoclonal anti-HMGB1 antibody (5 μg/mouse, injected IP at 2 and 7 hours post-APAP) and euthanized at 24 hours post-APAP. The third set of experiments was used to assess the efficacy of P5779 in APAP model in wild type mice. Male C57BL/6 mice received APAP injection plus P5779 (at 50 or 500 μg/mouse) or scrambled control peptide (500 μg/mouse, i.p. injected at 2 and 7 hours post-APAP) and euthanized at 24 hours post-APAP. In survival experiments, mice had injection of APAP and received treatment of P5779 or control peptide (500 μg/mouse, i.p. once a day for 5 days starting at 2 hours post-APAP) and survival was monitored for 2 weeks. Hepatotoxicity was determined by serum levels of glutamate dehydrogenase (GLDH), alanine aminotransferease (ALT) and aspartate aminotransferase (AST) as described previously. Antoine et al., Hepatology 58:777-787 (2013).

Histological evaluation. Harvested livers were fixed in 10% formalin, and embedded in paraffin. Five-µM sections were stained with hematoxylin and eosin. H&E staining of livers was performed by AML laboratory (Baltimore, Md.). The liver histology was evaluated in a blinded fashion and clinical scores were calculated based on the amount of necrosis and inflammation (cell swelling, loss of tissue structure, congestion) using a previously reported method with modifications. Desmet et al., Journal of hepatology 38:382-386 (2003). Score 0=no evidence of necrosis or inflammation as assessed from three to four representative sections from each animal; 1=mild necrosis or inflammation <25% of the total area examined, 2=notable necrosis and inflammation (25-50% of the total area); 3=severe necrosis and inflammation (>50% area).

Statistical analysis. Data are presented as means+SEM unless otherwise stated. Differences between treatment groups were determined by Student's t-test, one-way ANOVA followed by the least significant difference test. Differences between groups in animal survival studies were determined using two-tailed Fisher's exact test. Cytokine array studies were analyzed using the software UN-Scan-it from Silk scientific Inc. (Orem, Utah). P values less than 0.05 are considered statistically significant.

Example 2: Novel Strategies for Targeting Innate Immune Responses to Influenza

We previously reported that TLR4−/− mice are refractory to mouse-adapted A/PR/8/34 (PR8) influenza-induced lethality and, conversely, that therapeutic administration of the TLR4 antagonist, Eritoran, blocked PR8-induced lethality and acute lung injury (ALI). Herein, we extend these findings: anti-TLR4- or TLR2-specific IgG therapy also conferred significant protection of wild-type (WT) mice from lethal PR8 infection. If initiated 3 h prior to PR8 infection and continued daily for 4 days, Eritoran failed to protect WT and TLR4−/− mice from lethality, implying that Eritoran must block a virus-induced, non-TLR4 signal that is required for protection. Mechanistically, we determined that (i) Eritoran blocks HMGB1-mediated, TLR4-dependent signaling in vitro and circulating HMGB1 in vivo, and an HMGB1 inhibitor protects against PR8; (ii) Eritoran inhibits pulmonary lung edema associated with ALI, (iii) IL-1β contributes significantly to PR8-induced lethality, as evidenced by partial protection by IL-1 receptor antagonist (IL-1Ra) therapy. Protection against PR8-induced lethality was achieved when Eritoran and oseltamivir were administered starting on day 4 post-infection. Eritoran treatment does not prevent development of an adaptive immune response to subsequent PR8 challenge. Overall, our data support the potential of a host-targeted therapeutic approach to influenza infection.

Results

We previously reported that TLR4$^{-/-}$ mice were refractory to mouse-adapted influenza, PR8 (Nhu et al., Mucosal Immunol. 3, 29-39 (2010)), and have now confirmed that TLR4$^{-/-}$ mice are also refractory to a more pathogenic, mouse-adapted pandemic H1N1 strain, ma.Ca/04. Ye et al., PLoS Pathog. 6, e1001145 (2010). We also showed previously that treatment of PR8-infected, WT mice therapeutically with the TLR4 antagonist, Eritoran, significantly protected against lethality, and attenuated ALI, findings confirmed in C57BL/6 mice infected with the ma.Ca/04 strain. Eritoran also protected PR8-infected BALB/c mice (data not shown). Finally, we found that an additional daily dose of Eritoran (i.e., administered once vs. twice daily), starting four days post-infection, failed to improve protection achieved with a single dose daily (data not shown). Together, these data underscore our previous observations that therapeutic treatment of mice with Eritoran protects against lethality with additional influenza strains and under different conditions of infection. The following experiments were designed to provide mechanistic insights into Eritoran-mediated protection and to identify new pathways that contribute to influenza-induced disease that are affected by Eritoran treatment.

Figure 7:
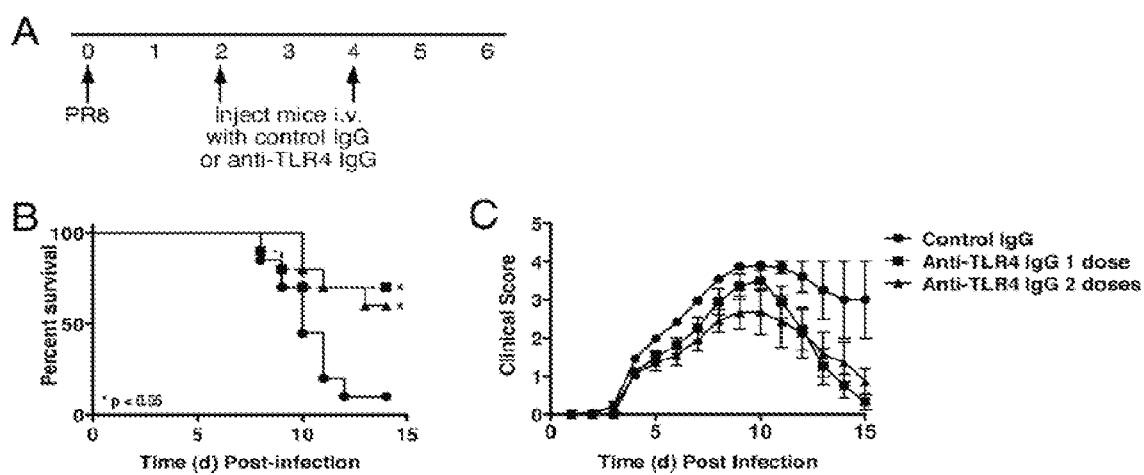
FIGS. 7A-7C provide graphs showing anti-TLR4 IgG treatment protects mice from lethal influenza challenge. (A) C57BL/6J mice were infected with mouse-adapted influenza strain PR8 (7500 $TCID_{50}$, i.n.; ~$LD_{90}$). Mice received either control IgG or a highly specific anti-TLR4 IgG (2 mg/mouse i.v.) once (day 2 only) or twice (days 2 and 4). Survival (B) and clinical scores (C) were monitored daily. Each graph represents the combined results of 2 separate experiments (5 mice/treatment group/experiment).

Elucidation of Signaling Requirements Underlying Influenza-Induced Lethality and Protection by Eritoran Eritoran blocks TLR4 signaling by binding in the deep hydrophobic pocket of its co-receptor, MD2, thereby blocking ligand-induced dimerization. Kim et al., Cell 130, 906-917 (2007). To validate the role of TLR4 in PR8-induced lethality, mice were treated with a highly specific anti-TLR4 antibody Roger et al., Proc. Natl. Acad. Sci. USA 106, 2348-2352 (2009) (FIG. 7A). Anti-TLR4 IgG, but not an isotype-matched control IgG, administered on day 2 only or on days 2 and 4 post-PR8 infection i.v., protected mice against lethal infection (FIG. 7B) and elicited significantly improved clinical scores (p<0.004 FIG. 7C). This result confirms that, indeed, TLR4 signaling is central to influenza-induced lethality and clinical symptoms.

Figure 8:
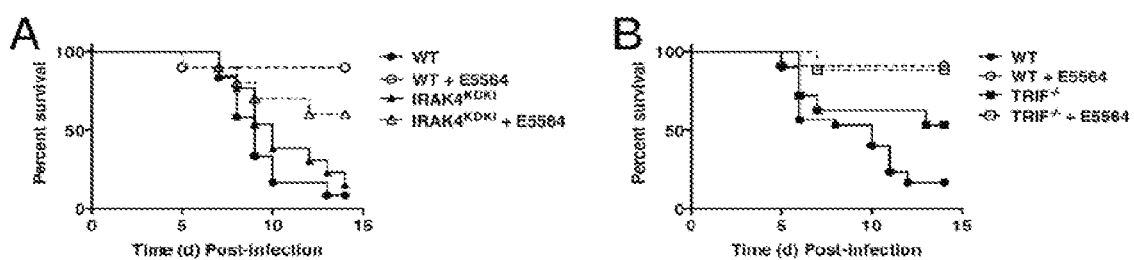
FIGS. 8A and 8B provide graphs showing the effect of Eritoran on IRAK4$^{KDKI}$ and TRIF$^{-/-}$ mice. WT C57BL/6J (A and B), IRAK4$^{KDKI}$ (A) and TRIF$^{-/-}$ (B) mice were infected with mouse-adapted influenza strain PR8 (~7500 $TCID_{50}$, i.n.; ~$LD_{90}$). Mice received either vehicle (saline; i.v.) or Eritoran (E5564; 200 µg/mouse; i.v for 5 consecutive days starting on day 2 post-infection. Survival was monitored for 14 days. Data shown is combined results of 2-3 separate experiments (5-10 mice/treatment group/experiment).

TLR4 is the only TLR that activates both the MyD88- and TRIF-dependent signaling pathways. One of the central conclusions of Imai et al. was that TLR4-mediated ALI induced by inactivated H5N1 influenza or the host-derived oxidized phospholipid, OxPAPC, is entirely TRIF-dependent. However, MyD88 has been strongly implicated in the host response to influenza. Teijaro et al., J. Immunol. 82, 6834-43 (2009). IRAK4, the first enzyme recruited to MyD88, initiates signaling leading to IKKα/β/γ complex activation, IκBα phosphorylation, and ultimately, NF-κB activation. The TRIF pathway drives IRF3 activation and results in delayed NF-κB activation, but this latter pathway does not employ IRAK4 to activate the IKK complex. To delineate the downstream pathway(s) underlying the host response to influenza and the protective mechanisms of Eritoran, we assessed PR8 lethality and the efficacy of Eritoran in IRAK4 kinase dead knock-in (IRAK4$^{KDKI}$) mice, that have a catalytically inactive form of IRAK4 that blocks MyD88-dependent signaling, vs. TRIF$^{-/-}$ mice. IRAK4$^{KDKI}$ mice exhibited a slightly delayed mean time to death compared to WT mice, and Eritoran therapy resulted in ~60% survival compared to ~90% in WT mice (FIG. 8A). Interestingly, TRIF$^{-/-}$ mice were more resistant to PR8 infection than WT or IRAK4$^{KDKI}$ mice (~50% survival), but not as refractory as TLR4$^{-/-}$ mice. Nhu et al., Innate Immun 18, 193-203 (2012). However, treatment with Eritoran significantly improved their survival to WT levels (p<0.001; FIG. 8B). VIPER is an 11 amino acid peptide derived from the A46 protein of Vaccinia virus that has been shown to bind to TRIF and block TRIF-dependent signaling. Lysakova-Devine et al., J. Immunol. 185, 4261-71 (2010). When WT mice were infected with PR8 and treated therapeutically with either a cell-permeating VIPER peptide, 9R-VIPER, or Eritoran, 9R-VIPER treatment resulted in partial protection (50%), consistent with the degree of protection seen in TRIF$^{-/-}$ mice (FIG. 8B). Together, both MyD88- and TRIF-dependent pathways contribute to influenza-mediated disease and Eritoran-induced protection.

Figure 9:
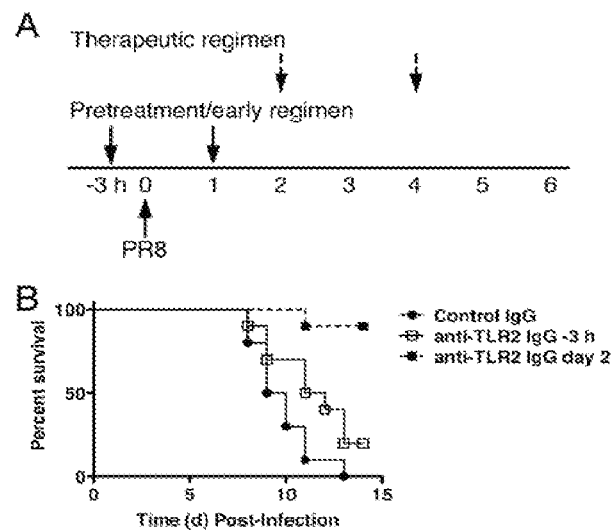
FIGS. 9A and 9B provide graphs showing anti-TLR2 IgG treatment protects mice from lethal influenza challenge. (A) Experimental protocol. C57BL/6J mice were either treated with isotype control IgG or anti-TLR2 (T2.5; 100 µg/ms i.v.) 3 h prior to and 1 day post-infection or on days 2 and 4 post-infection. Survival (B) was monitored daily. Data shown is combined results of 2 separate experiments (5 mice/treatment group/experiment).

We reported previously that TLR2$^{-/-}$ mice were comparably sensitive to WT mice for PR8-induced lethality. However, unlike WT mice, Eritoran therapy failed to protect TLR2$^{-/-}$ mice; thus, TLR2 was presumed to be a direct or indirect target for Eritoran. To confirm the role of TLR2 in influenza-induced disease, we used a monoclonal antibody directed against TLR2 (clone T2.5) that blocks signaling in vivo. Meng et al., J. Clin. Invest. 113, 1473-1481 (2004). Groups of mice were either treated with anti-TLR2 or with an isotype control antibody 3 h prior and 1 day post-PR8 infection, while two other groups received anti-TLR2 or control antibody on days 2 and 4 post-PR8 infection (FIG. 9A). Similar to with the protection achieved with anti-TLR4 IgG (FIG. 7), treatment of PR8-infected WT mice with anti-TLR2 antibody significantly protected against lethality when administered on days 2 and 4 post-infection (p<0.001; FIG. 9B); however, anti-TLR2 treatment was not effective when administered earlier. These results suggest the presence of a TLR2 agonist released late after PR8 infection that contributes to lethality.

Figure 10:
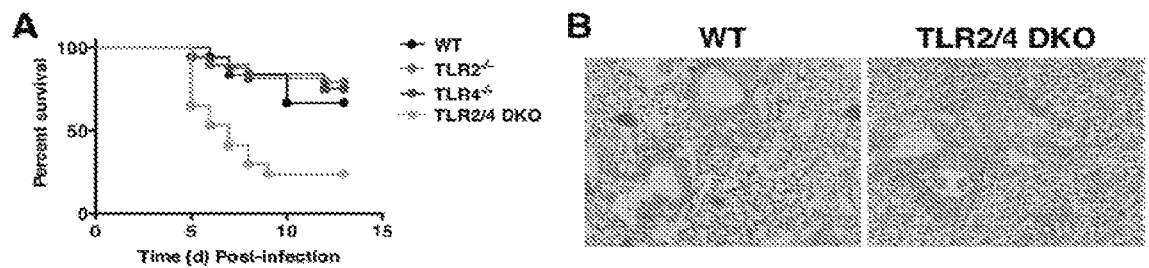
FIGS. 10A and 10B provide a graph and image showing TLR2/TLR4 double knockout mice are more sensitive to influenza infection. (A) C57BL/6J WT, TLR2$^{-/-}$, and TLR4$^{-/-}$ and TLR2/TLR4 double knockout mice (TLR2/4) mice were infected with mouse-adapted influenza strain PR8 (~40,000 pfu, i.n.; ~$LD_{10}$ in WT mice). Mice were monitored for survival daily for 14 days. Data shown is combined from two separate experiments (4-12 mice/group/experiment). (B) WT, TLR2$^{-/-}$, and TLR2/4 double knockout mice were infected as in (A). Lungs were harvested on day 5 post-infection for histopathology. Data shown is representative lung section (3-4 mice/group).

To extend these findings, WT, TLR2$^{-/-}$, TLR4$^{-/-}$, and TLR2/4 double knockout mice were infected with a sublethal dose of PR8 and monitored for 14 days. The TLR2/4 double knockout mice were much more susceptible than the WT or individual knockout mice (FIG. 8A). Specifically, ALI was significantly worse in TLR2/4 double-knockout mice than in WT, with inflammatory infiltrates throughout the parenchyma and alveolar spaces (composed of neutrophils and lymphocytes) (FIG. 10B). These findings suggest that a TLR2 agonist induced early in virus infection is necessary for the resistance of TLR4$^{-/-}$ mice to lethal PR8 infection.

Timing of Eritoran treatment is Critical for Protection

Figure 11:
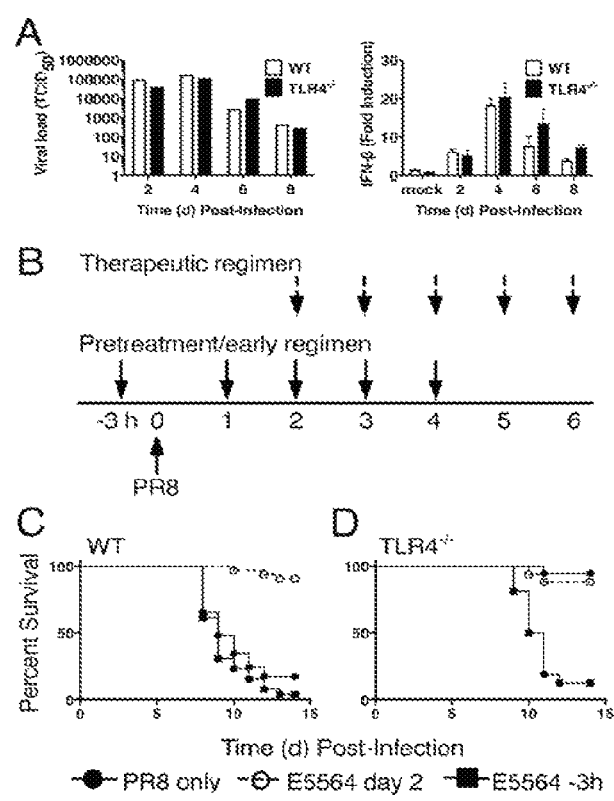
FIGS. 11A-11D provide graphs showing pretreatment of WT or TLR4$^{-/-}$ mice with Eritoran does not protect from lethal influenza challenge. (A) WT and TLR4$^{-/-}$ mice were infected with mouse-adapted influenza strain PR8 (~7500 $TCID_{50}$, i.n.) and sacrificed on days 2, 4, and 6 post-infection. Lungs were harvested and assayed for viral titers and IFN-β mRNA. Data shown is combined results of 2 separate assays (4-5 mice/group/experiment). (B) Basic experimental protocol used to compare pretreatment/early vs. therapeutic treatment with Eritoran in PR8-infected mice. C57BL/6J WT and TLR4$^{-/-}$ mice were either untreated (solid circles), or treated with Eritoran starting 3 h prior to infection and on day 1 for 4 successive days (3 h; solid squares; pretreatment/early regimen), or starting 2 days after infection for 5 successive days (open circles; therapeutic regimen). (C and D) Mice were monitored daily for survival. The data represent the combined results of two separate experiments (5-6 mice/treatment/experiment).

Neither differential influenza replication nor the levels of inducible IFN-β mRNA induced could account for the resistance of the TLR4$^{-/-}$ mice to PR8 infection (FIG. 11A). Eritoran therapy protected PR8-infected WT mice (FIGS. 11B and 11C, open circle, left panel), but did not affect the resistance of TLR4$^{-/-}$ mice (FIGS. 11B and 11D; open circle, right panel), as we reported previously. Shirey et al., Nature 497, 498-502 (2013). However, when Eritoran treatment was initiated prophylactically (3 h prior to PR8 infection) and continued daily for an additional 4 days (FIG. 11B, pretreatment/early regimen; closed squares), WT mice were not protected from lethality (FIG. 11C, closed square, left panel). This implies that an early influenza-inducible, but late-acting mediator of lethality and ALI must be the target of Eritoran in WT mice. Surprisingly, this identical regimen rendered TLR4$^{-/-}$ mice susceptible to PR8 infection (FIGS. 11B and 11D, closed square, right panel), indicating that a non-TLR4 target of Eritoran is necessary for the resistance of TLR4$^{-/-}$ mice to PR8 infection, consistent with our data obtained with the TLR2/4 double knockout mice. Pretreatment/early Eritoran had no effect on the susceptibility of CD14$^{-/-}$ or TLR2$^{-/-}$ mice.

P5779, an MD2 Antagonist, Blocks Influenza-Mediated Lethality

Figure 12:
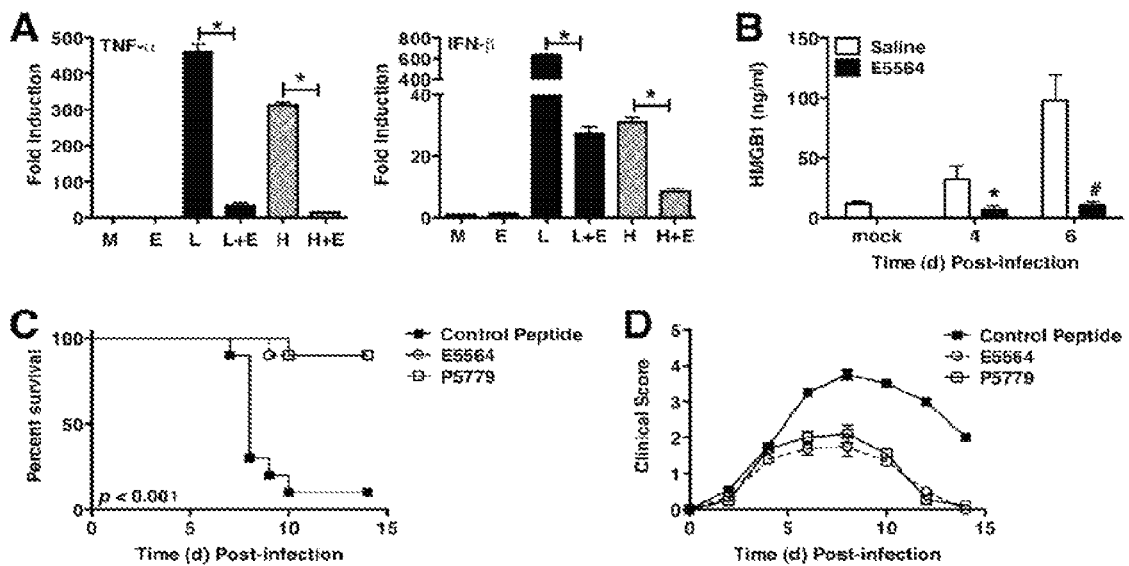
FIGS. 12A-12D provides graphs showing Eritoran blunts HMGB1-induced TLR4 signaling in vitro and influenza-induced HMGB1 release and lethality in vivo. (A) Thioglycollate-elicited C57BL/6J macrophages were treated with medium alone (M) or Eritoran (E; 10 ng/ml) for 1 h, and then with LPS (L; 10 ng/ml) or HMGB1 (H; 1 µg/ml) for 2 h. Total RNA was processed and subjected to qRT-PCR for detection of TNFα or IFN-β mRNA expression. (B) Cotton rats (6-8/time point/treatment) were infected with pdH1N1 A/California/04/09 ($10^6$ $TCID_{50}$ by i.n.), then treated with Eritoran or placebo starting at 6 h post-infection. Serum HMGB1 levels were measured by ELISA (*$p<0.05$). (C) C57BL/6J mice were infected were infected with mouse-adapted influenza strain PR8 (7500 $TCID_{50}$, i.n.; ~$LD_{90}$). Mice received either control peptide (500 µg/mouse; i.p.), Eritoran (E5564; 200 µg/mouse; i.v.), or the HMGB1 peptide, P5779 (500 µg/mouse; i.p.) for 5 consecutive days starting on day 2 post-infection (days 2-6). Survival (C) and clinical scores (D) were monitored daily for 14 days. Data shown is combined from 2 experiments (5-10 mice/treatment group/experiment).

We previously reported that lungs of Eritoran-treated, PR8-infected mice (as shown in FIG. 7A) showed blunted cytokine induction as well as accumulation of OxPAPC, a DAMP shown by Imai et al. to mediate ALI by its action on macrophages through TLR4. Imai et al., Cell 133, 235-249 (2008). High Mobility Group B1 (HMGB1), a DAMP first implicated in endotoxicity and Gram negative sepsis, has been reported to be released during severe influenza infection (Alleva et al., J. Immunol. 181, 1454-1459 (2008)) and activates TLR4 by binding to the TLR4 co-receptor, MD2. Yang et al., J. Leukoc. Biol. 93, 865-873 (2013). HMGB1-stimulated WT murine macrophages induced MyD88- and TRIF-dependent gene expression that was inhibited by Eritoran in vitro (FIG. 12A). Mice infected with PR8 and cotton rats infected with a non-adapted human influenza pdH1N1 strain, exhibited increased circulating HMGB1 that was inhibited by Eritoran treatment in vivo (FIG. 12B). Thus, HMGB1, like OxPAPC, may represent a DAMP that is released relatively late after infection that contributes to influenza-induced ALI through TLR4 activation. P5779 is a small molecule inhibitor of HMGB1 that was shown recently to prevent MD2/HMGB1 interaction and block HMGB1-induced TLR4 signaling, while not interfering with LPS-induced cytokine/chemokine induction. P5779 protected mice against hepatic ischemia/reperfusion injury, chemical toxicity, and sepsis. Yang et al., Exp. Med. 212, 5-14 (2015). To assess the efficacy of P5779 in influenza infection, WT C57BL/6J mice were infected with PR8 and, two days later mice were treated with either Eritoran (E5564), an inactive control peptide, or P5779 for 5 consecutive days. Both Eritoran and P5579 treatment of mice showed significant survival and lowered clinical scores, while mice treated with the control inhibitor showed higher clinical scores and succumbed to infection (FIGS. 12C, D).

A PAR2 Antagonist Blocks Influenza-Induced Lethality and Lung Leak

Figure 13:
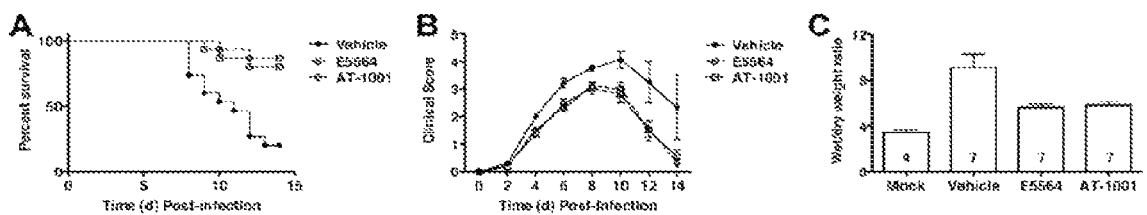
FIG. 13A-13C provide graphs showing the Effect of AT-1001 against lethal influenza challenge. (A) C57BL/6J mice were infected with mouse-adapted influenza strain PR8 (~7500 $TCID_{50}$, i.n.; ~$LD_{90}$). Mice received either vehicle (saline; i.v.), Eritoran (E5564; 200 μg/mouse; i.v.), or AT-1001 (150 μg/mouse; i.v.) for 5 consecutive days starting on day 2 post-infection (days 2-6). Survival (A) and clinical scores (B) were monitored daily for 14 days. Data shown is combined from 3 separate experiments (5 mice/treatment group/experiment). (C) Lung wet-to-dry (W/D) weight ratio as an index for pulmonary edema after infection. C57BL/6J mice were infected and treated as described above. On day 7 post-infection, lungs were harvested and lung weights were measured immediately after excision and recorded as wet weight. Lung tissue was air dried for 5-6 days and re-weighed until a stable dry weight obtained. The W/D weight ratio was calculated by dividing the wet by dry weight. The N for each group is indicated in each bar. Each vertical bar represents the mean (±s.e.m.).
Figure 14:
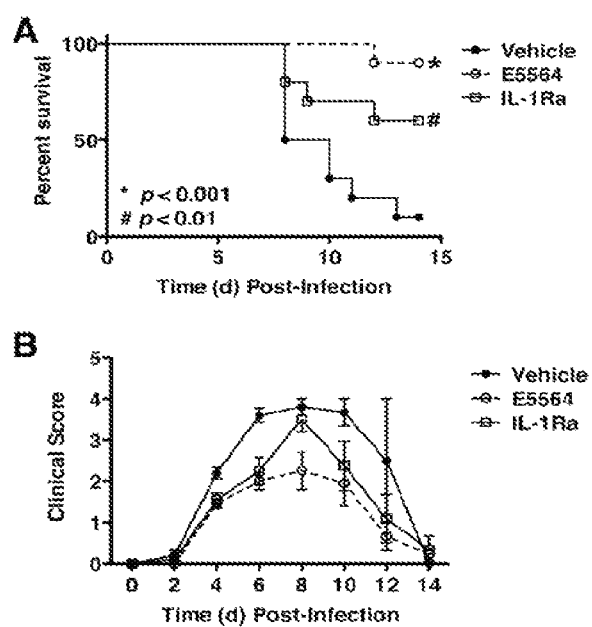
FIGS. 14A and 14B provide graphs showing the effect of IL-1Ra against lethal influenza challenge. C57BL/6J mice were infected with mouse-adapted influenza strain PR8 (~7500 $TCID_{50}$, i.n.; ~$LD_{90}$). Mice received either vehicle (saline; i.v.), Eritoran (E5564; 200 μg/mouse; i.v.), or the IL-1Ra (150 μg/mouse; i.v.) for 5 consecutive days starting on day 2 post-infection (days 2-6). Survival (top panel) and clinical scores (bottom panel) were monitored daily for 14 days. Data shown is combined from 2 separate experiments (5 mice/treatment group/experiment).

A host-derived protein, originally called zonulin (now known to be pre-haptoglobin 2), was found to increase intestinal permeability by phosphorylation of tight junction proteins. Goldblum et al., FASEB J. 25, 144-158 (2011). Signaling was dependent upon protease-activated receptor 2 (PAR$_2$), a signaling protein that we have shown previously to interact physically and functionally with TLR4. A zonulin analog peptide antagonist, AT-1001 (larazotide acetate), is well-tolerated in humans and attenuates gut inflammation associated with celiac disease. Recently, AT-1001 was also reported to attenuate ALI in mice induced by intrapulmonary deposition of IgG immune complexes or LPS by inhibiting ZO-1 phosphorylation and reducing the number of leukocytes and myeloperoxidase activity in bronchoalveolar lavage fluid (BALF). Rittirsch et al., Am. J. Physiol. Lung Cell. Mol. Physiol. 304, L863-72 (2013) Since both PAR2$^{-/-}$ and TLR4$^{-/-}$ mice are comparably refractory to lethal PR8 infection, we compared the efficacy of AT-1001 vs. Eritoran therapy during a lethal influenza challenge. WT mice were infected with PR8 and treated with vehicle (saline), Eritoran, or AT-1001 for 5 consecutive days starting on day 2 post-infection. Treatment of mice with AT-1001 resulted in significant protection and lowered clinical scores, comparably to Eritoran treatment (FIGS. 13A, B). Since the AT-1001 reduced the pulmonary edema associated with LPS- or immune complex-induced ALI, we tested whether Eritoran and AT-1001 mediated a decrease in lung edema caused by PR8 infection as measured by wet-to-dry (W/D) weight ratio. Mice infected with PR8 and treated with vehicle showed higher W/D ratios than mice infected with PR8 and treated with either Eritoran or AT-1001 (FIG. 13C), suggesting that an additional protective effect of Eritoran during influenza infection is to attenuate ALI by blunting pulmonary edema.

Contribution of IL-1β to Influenza-Induced Lethality

We previously showed that IL-1β mRNA is strongly inhibited in the lungs of PR8-infected, Eritoran-treated mice. Subsequently, Teijero et al. reported that influenza-infected IL-1R$^{-/-}$ mice exhibited diminished cytokine levels in the BALF 2 days p.i. (Teijaro, J. R. et al. J. Immunol. 82, 6834-43 (2009)), but neither ALI nor lethality were evaluated. rIL-1 receptor antagonist (IL-1Ra; a.k.a. Kineret, anakinra) is used clinically to treat highly inflammatory diseases (e.g., rheumatoid arthritis, cryopyrin-associated periodic syndromes). Dinarello et al., Nat. Rev. Drug Discov. 11, 633-652 (2012). PR8-infected C57BL/6J WT mice treated therapeutically with rIL-1Ra showed significant, but intermediate, survival (FIG. 8A), and clinical scores (FIG. 8B), in contrast to the protection afforded by Eritoran. This suggests that while IL-1β participates in mediating influenza-induced disease, other mediators, whose action is inhibited by Eritoran, are also involved.

Eritoran Treatment Improves the Efficacy of Oseltamivir Therapy Against Influenza The efficacy of Eritoran administered alone or combined with the approved neuraminidase inhibitor antiviral therapy, Tamiflu™ (oseltamivir), was assessed. To be effective, oseltamivir treatment is recommended within 2 days after the onset of symptoms. Khazeni et al., Ann. Intern. Med. 151, 464-473 (2009). Since, in our model, mice show clinical symptoms starting at day 3 post-infection, we compared mice treated with vehicle, Eritoran alone, Oseltamivir alone, or both Eritoran and Oseltamivir starting on days 2, 4, or 6 post-infection for 5 consecutive days. When treatment was initiated on day 2 post-infection, both agents were highly protective, with no benefit when administering together. However, when administration of treatment was delayed until 4 or 6 days post-infection, treatment with oseltamivir alone showed little protective effect (particularly when administered starting at Day 6), while the Eritoran still elicited a significant degree of protection from lethality, as we reported previously. Importantly, when initiated on day 4, the combined Eritoran/oseltamivir treatment resulted in a significant improvement in survival. This is consistent with Zheng et al. who showed co-administration of celecoxib, a COX-2 inhibitor, and zanamivir improved survival of influenza-infected mice better than treatment with zanamivir alone. Zheng et al., Proc. Natl. Acad. Sci. USA 105, 8091-8096 (2008). Our previous study showed that Eritoran blunts COX-2 induction during influenza infection.

Survivors of PR8 Infection After Eritoran Treatment Develop Adaptive Immunity

Importantly, mice that were protected from PR8 by Eritoran survived secondary PR8 challenge 2 weeks later, without additional Eritoran therapy. Thus, the anti-inflammatory effect of Eritoran during primary infection does not impair development of an adaptive immune response against influenza.

Discussion

Influenza is a major health concern globally. The virus mutates rapidly, leading to anti-viral resistance or altered expression of immunogenic epitopes such that extant vaccines are rendered ineffective. Based on our previous studies (Nhu et al., Mucosal Immunol. 3, 29-39 (2010)), we postulated that Eritoran (E5564), a well-tolerated, synthetic TLR4 antagonist (Kalil et al., Shock 36, 327-331 (2011)), represents a novel therapeutic approach to ameliorate influenza-induced ALI by blocking TLR-mediated signaling in response to host-derived DAMPs. Herein, we delineate further the cellular and molecular underpinnings for both induction of ALI and its abatement by Eritoran therapy.

Our data show that Eritoran therapy does not alter the refractoriness of TLR4$^{-/-}$ mice to influenza infection; both Eritoran and anti-TLR4 antibody therapy protected WT mice, and, Eritoran binds to both CD14 and MD2 in vitro (Shirey et al., Nature 497, 498-502 (2013)), both of which are required for TLR4 signaling. Together, these findings strongly implicate TLR4 in both influenza-induced disease and as a target for Eritoran-mediated protection. Since Eritoran pretreatment/early regimen renders TLR4$^{-/-}$ mice susceptible, Eritoran must also interact with a non-TLR4 PRR that is required early for induction of resistance. Since CD14 can act as a co-receptor for TLR2, TLR3, TLR7, and TLR9, and since the latter three have been implicated in the host response to influenza (Leung et al. J. Gen. Virol. 95, 1870-1879 (2014)) and are capable of inducing IFN-β (Kawai et al., Nat. Immunol. 11, 373-384 (2010)) we postulate that Eritoran, administered by the pretreatment/early regimen, binds CD14 and inhibits transfer of specific PAMPs or DAMPs to one or more of these TLRs to induce IFN-β. This hypothesis is supported by our observation that WT and TLR4$^{-/-}$ mice, given Eritoran by the early regimen, are as susceptible as IFN-β$^{-/-}$ mice to PR8 infection, and that CD14$^{-/-}$ mice could not be protected by Eritoran pretreatment/early or therapeutic regimens, presumably because they cannot produce cytokines as suggested by Pauligk et al (Immunobiology 209, 3-10 (2004)).

The role of TLR2 in Eritoran-mediated protection of PR8-infected mice is more enigmatic. Despite the fact that we observed that anti-TLR2 MAb, but not control IgG, protected WT mice from PR8 when administered therapeutically, the same anti-TLR2 MAb, when administered −3 h prior to and 1 day after PR8 infection, provided only minimal protection. This strongly suggests that TLR2, like TLR4, also plays a damaging role later in infection. OxPAPC (Kadl et al., Free Radic. Biol. Med. 51, 1903-1909 (2011)) and HMGB1 (Yang et al., J. Leukoc. Biol. 93, 865-873 (2013)) have been reported to be both TLR2 and TLR4 agonists that are induced later in infection. These DAMPs may synergize to increase TLR2 expression and/or TLR2-dependent signaling. Our observation that TLR2/4 double knockout mice were highly susceptible to sublethal PR8 infection may suggest that the absence of both TLR2 and TLR4 would leave MyD88 more available for IL-1 and IL-18 signaling. Alternatively, it could also mean that TLR2 is required to produce something that mediates resistance to PR8 in TLR4$^{-/-}$ mice.

Eritoran blunts both the influenza-induced "cytokine storm" and the accumulation of OxPAPC, an oxidized phospholipid TLR4 DAMP. Mechanistically, these findings have now been extended by showing that Eritoran (i) blocked HMGB1-mediated, TLR4-dependent signaling in vitro, HMGB1 release into serum in vivo, and protected comparably to P5779, a highly selective HMGB1 inhibitor; and (iii) inhibited pulmonary lung edema equivalently to AT1001, an inhibitor of zonulin-induced pulmonary edema. The latter effect of Eritoran therapy correlates with increased lung function we showed previously compared to untreated, influenza-infected mice. A recent study showed a possible link between TLR4 activation in the gut from trauma/hemorrhagic shock and the development of ALI by suggesting that increased paracellular permeability in intestinal epithelium results in lung injury. Sodhi et al., J. Immunol. 194, 4931-4939 (2015). Additionally, the partial protection achieved by treatment of PR8-infected mice supports a role for IL-1 signaling in PR8-induced lethality, however, supports a role for other inflammatory mediators in PR8-induced disease. Our observation that Eritoran-induced protection did not prevent development of an adaptive immune response influenza warrants future studies to evaluate the effect of Eritoran on influenza-induced, enhanced sensitivity to secondary bacterial infections. Overall, our findings underscore the complex nature of microbe-host inflammatory cell interactions that control the host's ability to respond to invading virus. We provide evidence that multiple receptors on innate immune cells are likely involved; however, it is also likely that unknown interactions among these receptors in response to microbial and host ligands significantly affect, both qualitatively and quantitatively, the host response.

Methods

Reagents

Eritoran (E5564) was kindly provided by Eisai Inc. (Andover, Mass.) and was prepared as described previously. Shirey et al., Nature 497, 498-502 (2013). *Escherichia coli* K235 LPS was prepared as previously described. McIntire et al., Biochemistry 6, 2363-2376 (1967). The anti-TLR2 IgG and isotype control IgG were purchased from Affymetrix (Santa Clara, Calif.). Recombinant HMGB1 was provided by Kevin Tracey (Feinstein Institute for Medical Research, Manhasset, N.Y.). 9R-VIPER was kindly provided by Andrew Bowie (Trinity College, Ireland). P5779 and control peptide were kindly provided by Yousef Al Abed (Feinstein Institute for Medical Research, Manhasset, N.Y.). The anti-TLR4 IgG and isotype control IgG were kindly provided by Thierry Roger and Thierry Calandra (Infectious Diseases Service, Centre Hopsilalier Universitaire Vaudois and University of Lausanne, Lausanne, Switzerland). AT-1001 was kindly provided by Alessio Fassano (Division of Pediatric Gastroenterology and Nutrition, MGH, Boston, Mass.). IL-1Ra was kindly provided by Charles Dinarello (University of Colorado, Colo.).

Mice and Cotton Rats

Six to 8-week old, WT C57BL/6J mice were purchased (The Jackson Laboratory, Bar Harbor, Me.). All mice with targeted mutations were bred onto or derived directly from a C57BL/6 background. TLR4$^{-/-}$ mice (originally provided by Shizuo Akira, Osaka, Japan; bred at UMB (Baltimore, Md.) and Univ. Massachusetts Medical School, (Worcester, Mass.)), TRIF$^{-/-}$ (bred at U. Mass. Med. School), IRAK4$^{KDKI}$ (provided by Lilly Research Laboratories, Indianapolis, Ind., bred at UMB), TLR2$^{-/-}$ mice (provided by Shizuo Akira; bred at U. Massachusetts Medical School), and TLR2/TLR4 double knockout mice (bred at U. Mass. Medical School (Worcester, Mass.)). BALB/cByJ mice were purchased from Jackson Laboratories (Bar Harbor, Me.). All mouse strains were housed and bred in specific pathogen-free conditions. Experiments were conducted in accordance with the guidelines set forth by the University of Maryland, Baltimore and the University of Massachusetts Medical School Department of Animal Medicine and approved by each institute's Institutional Animal Care and Use Committees (IACUC).

Inbred young adult (4-8 weeks old) cotton rats (*Sigmodon hispidus*) were bred at Sigmovir Biosystems, Inc. (Rockville, Md.). All cotton rat experiments were conducted with Institutional Animal Care and Use Committee (IACUC) approval from Sigmovir Biosystems, Inc.

Virus

Mouse-adapted H1N1 influenza A/PR/8/34 virus ("PR8") (ATCC, Manassas, Va.) was grown in the allantoic fluid of 10-day old embryonated chicken eggs as described (Teijaro et al., J. Immunol. 82, 6834-43 (2009)) and was kindly provided by Dr. Donna Farber (Columbia University, N.Y.). Mouse-adapted H1N1 influenza maCa.04 was provided by Daniel Perez (Georgia State University, Atlanta, Ga.). Non-adapted human influenza virus strain pH1N1 was obtained and grown as previous described. Blanco et al., J. Virol. 87, 2036-45. (2013).

Virus Challenge and Treatments

Mice were infected with mouse-adapted influenza virus, strains A/PR/8/34 (PR8; ~7500 TCID$_{50}$, i.n., 25 µl/nares) or maCa.04 (2200 TCID$_{50}$, i.n.). Two days after infection, mice received either placebo or E5564 (Eritoran; 200 µg/mouse in 100 i.v.), anti-TLR4 IgG (2 mg/mouse, i.v.) or its isotype control IgG, anti-TLR2 (T2.4 clone; 100 µg/mouse, i.v.) or its isotype control IgG, P5779 or its control peptide (500 µg/mouse, i.p.), AT-1001 (150 µg/mouse, i.v.), IL-1Ra (150 µg/mouse, i.v.), or Oseltamivir (1 mg/mouse, p.o.) daily (Day 2 to Day 6). In some experiments, groups of mice were treated with Eritoran or Oseltamivir starting at day 4 or day 6 post-infection and treated for 5 successive days. In some experiments, some groups of mice were treated with E5564 (200 mg/mouse, i.v.) 3 h prior to infection with PR8 and then treated for 4 consecutive days starting day 1 post-infection (days 1-5). In some experiments, groups of mice were treated with anti-TLR2 (T2.5 clone, 100 µg/mouse, i.v.) or its control isotype IgG 3 h prior to infection with PR8 and then treated for a second time at day 1 post-infection for a total of two treatments. Mice were monitored daily for survival, weight loss, and clinical signs of illness (e.g., lethargy, piloerection, ruffled fur, hunched posture, rapid shallow breathing, audible crackling) for 14 days. A clinical score ranging from 0 (no symptoms) to 5 (moribund) was ascribed to each mouse daily.

TLR2/4 Double Knockout Mouse Studies

C57BL/6J WT, TLR4$^{-/-}$, TLR2$^{-/-}$, and TLR2/4 double knockout mice were 8-12 weeks of age at the time of infection. Influenza A/PR/8/34 (Charles River Laboratories, Wilmington, Mass.) virus stocks were diluted in sterile phosphate buffered saline (PBS) and kept on ice prior to use. Mice were anesthetized with isoflurane and infected 40,000 pfu (30 µl by i.n.) per mouse. In two assays, mice were monitored for survival for 14 days post-infection. In another assay, mice were sacrificed on day 5 post-infection and the lungs harvested for pathology. Lungs were inflated in situ with 1 ml of formalin (10% formaldehyde) obtained from the University of Massachusetts Medical School Morphology Core. The inflated lungs were fixed for 24-48 h, after which they were transferred to PBS. Lungs were bisected vertically and processed for paraffin embedding by the University of Massachusetts Medical School Morphology Core. Slides were prepared and H&E stained for histological analysis.

Lung Wet-To-Dry Weight Ratio

The lung wet-to-dry (W/D) weight ratio was used as an index of pulmonary edema after infection with influenza in mice that were untreated or treated with either E5564 or AT-1001. On day 7 post-infection, mice were euthanized and dissected for the total lung, and the lung weight was measured immediately after excision (wet weight). Lung tissue was then air dried for 5-6 days and re-weighed every day until a dry weight was stable and this acted as the final dry weight. The W/D weight ratio was calculated by dividing the wet by the final dry weight.

Quantitative Real-Time PCR (qRT-PCR)

Total RNA isolation and qRT-PCR were performed as previously described. Shirey et al., J. Immunol. 181, 4159-4167 (2008). Levels of mRNA for specific genes are reported as relative gene expression normalized to mock-infected lungs.

Macrophage Cell Cultures and Treatment

Thioglycollate-elicited peritoneal macrophages from C57BL/6J WT mice were enriched as described after plating in 12-well ($2 \times 10^6$ cells/well) tissue culture plates. Shirey et al., J. Immunol. 181, 4159-4167 (2008). Macrophages were pre-treated with Eritoran (10 ng/ml) for 1 h and then stimulated with LPS (10 ng/ml) or HMGB1 (1 µg/ml) for 2 h.

HMGB1 Serum Levels

Cotton rats were inoculated with $9 \times 10^4$ TCID$_{50}$ of pH1N1 intranasally on day 0. On day 2 post-infection, animals were treated with saline (mock) or with 37.33 mg/kg of Eritoran, daily. Blood samples were collected on day 4 and on day 6 post-infection and serum was used for measuring HMGB1 levels were measured using an ELISA kit according to manufacturer's protocol (IBL International, Toronto, Ontario, Canada).

Statistics

Statistical differences between two groups were determined using an unpaired, two-tailed Student's t test with significance set at $p<0.05$. For comparisons between ≥3 groups, analysis was done by one-way ANOVA followed by a Tukey's multiple comparison test with significance determined at $p<0.05$. For survival studies, a Log-Rank (Mantel-Cox) test was used.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds are effective, the inventors are not bound by theories described herein. The invention is not limited to the exact details shown and described, for variations obvious to one skilled in the art will be included within the invention defined by the claims.

The invention claimed is:

1. A method of treating high-mobility group box protein B1 (HMGB1)-mediated inflammation in a subject, by administering a therapeutically effective amount of P5779 to the subject in need thereof, wherein P5779 is the tetrapeptide FSSE (SEQ ID NO: 1) and HMGB1 is the HMGB1 disulfide isoform.

2. The method of claim 1, wherein the HMGB1-mediated inflammation is caused by infection.

3. The method of claim 2, wherein the HMGB1-mediated inflammation is caused by viral infection.

4. The method of claim 3, wherein the HMGB1-mediated inflammation is caused by influenza infection.

5. The method of claim 3, further comprising administering an antiviral agent to the subject.

6. The method of claim 5, wherein the antiviral agent is oseltamivir.

7. The method of claim 2, wherein the HMGB1-mediated inflammation is caused by bacterial infection.

8. The method of claim 2, wherein P5779 is administered after the onset of infection.

9. The method of claim 1, wherein the HMGB1-mediated inflammation is caused by sterile injury.

10. The method of claim 1, wherein the HMGB1-mediated inflammation is caused by acetaminophen toxicity.

11. The method of claim 1, wherein the subject is human.

12. The method of claim 1, wherein P5779 is administered in a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 10,857,197 B2 | Page 1 of 1 |
| APPLICATION NO. | : 15/532226 | |
| DATED | : December 8, 2020 | |
| INVENTOR(S) | : Kevin J. Tracey et al. | |

It is certified that error appears in the above-identified patent and that said Letters Patent is hereby corrected as shown below:

On the Title Page

Item (71) Please remove "The Feinstein Institue for Medical Research"
Please insert -- The Feinstein Institute for Medical Research --

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: MD2 binding peptide

<400> SEQUENCE: 1

Phe Ser Ser Glu
1

<210> SEQ ID NO 2
<211> LENGTH: 5
<212> TYPE: PRT
<213> ORGANISM: Artificial Sequence
<220> FEATURE:
<223> OTHER INFORMATION: MD2 binding protein

<400> SEQUENCE: 2

Phe Ser Ser Glu Tyr
1               5

<210> SEQ ID NO 3
<211> LENGTH: 4
<212> TYPE: PRT
<213> ORGANISM: Artificial Sequence
<220> FEATURE:
<223> OTHER INFORMATION: MD2 binding protein
```

```
<400> SEQUENCE: 3

Phe Glu Glu Glu
1

<210> SEQ ID NO 4
<211> LENGTH: 4
<212> TYPE: PRT
<213> ORGANISM: Artificial Sequence
<220> FEATURE:
<223> OTHER INFORMATION: MD2 binding protein

<400> SEQUENCE: 4

Phe Glu Glu Asp
1

<210> SEQ ID NO 5
<211> LENGTH: 4
<212> TYPE: PRT
<213> ORGANISM: Artificial Sequence
<220> FEATURE:
<223> OTHER INFORMATION: MD2 binding protein

<400> SEQUENCE: 5

Ser Phe Ser Glu
1
```